(12) United States Patent
Cabrera et al.

(10) Patent No.: US 12,013,406 B2
(45) Date of Patent: Jun. 18, 2024

(54) METHODS OF DETECTING ANTI-FOLIC ACID ANTIBODIES AND USES THEREOF

(71) Applicant: Board of Regents, The University of Texas System, Austin, TX (US)

(72) Inventors: Robert M. Cabrera, Houston, TX (US); Richard H. Finnell, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/699,706

(22) Filed: Mar. 21, 2022

(65) Prior Publication Data

US 2022/0214365 A1  Jul. 7, 2022

Related U.S. Application Data

(62) Division of application No. 16/310,059, filed as application No. PCT/US2017/037404 on Jun. 14, 2017, now Pat. No. 11,313,868.

(60) Provisional application No. 62/349,960, filed on Jun. 14, 2016.

(51) Int. Cl.
| | |
|---|---|
| G01N 33/53 | (2006.01) |
| A61K 31/519 | (2006.01) |
| C07K 16/44 | (2006.01) |
| G01N 33/543 | (2006.01) |
| G01N 33/68 | (2006.01) |
| G01N 33/82 | (2006.01) |

(52) U.S. Cl.
CPC .......... *G01N 33/82* (2013.01); *A61K 31/519* (2013.01); *C07K 16/44* (2013.01); *G01N 33/54366* (2013.01); *G01N 33/6854* (2013.01); *G01N 2800/02* (2013.01)

(58) Field of Classification Search
None
See application file for complete search history.

(56) References Cited

U.S. PATENT DOCUMENTS

| | | | |
|---|---|---|---|
| 7,846,672 B2 | 12/2010 | Rothenberg | |
| 2003/0203412 A1 | 10/2003 | Vojdani | |
| 2006/0127955 A1* | 6/2006 | Rothenberg | G01N 33/564 |
| | | | 435/7.2 |
| 2009/0081710 A1 | 3/2009 | Low | |
| 2010/0179073 A1 | 7/2010 | Cabrera | |
| 2013/0267523 A1 | 10/2013 | Fava | |

FOREIGN PATENT DOCUMENTS

WO    2006119589 X    11/2006

OTHER PUBLICATIONS

Cabrera, RM et al., "Autoantibodies To Folate Receptor During Pregnancy And Neural Tube Defect Risk", J Reprod Immunol., (Apr. 14, 2014), vol. 79, pp. 1-14, XP025518889, 2014.
Christensen et al. (1999) "Genetic polymorphisms in methylenetetrahydrofolate reductase and methionine synthase, folate levels in red blood cells, and risk of neural tube defects," Am J Med Genet 84, 151-157.
Coppen, A et al., "Treatment Of Depression: Time To Consider Folic Acid And Vitamin B12", Journal of Psychopharmacology, (20050000), vol. 91, pp. 56-59, XP009168180, 2005.
Cragan et al. (1995) "Surveillance for anencephaly and spina bifida and the impact of prenatal diagnosis—United States, 1985-1994," MMWR CDC Surveill Summ 44, 1-13.
Czeizel A. E. and Dudas I. (1992) "Prevention of the First Occurrence of Neural-Tube Defects by Periconceptional Vitamin Supplementation," N Engl J Med 327, 1832-1835.
Dansky et al. (1992) "Mechanisms of teratogenesis: Folic acid and antiepileptic therapy," Neurology 42, 32-42.
Das Sarma et al., Antibody to folic acid: increased specificity and sensitivity in ELISA by using E-aminocaproic acid modified BSA as the carrier protein, Journal of Immunological Methods 184, 1995, pp. 1-6. (Year: 1995).
De Marco et al. (2000) "Folate pathway gene alterations in patients with neural tube defects," Am J Med Genet 95, 216-223.
Finnell et al. (2000) "Genetic basis of susceptibility to environmentally induced neural tube defects," Ann N Y Acad Sci. 919, 261-277.
Giles, C. (1966) "An account of 335 cases of megaloblastic anaemia of pregnancy and the puerperium," J Clin Path 19, 1-11.
Hernandez-Diaz et al. (2000), "Folic acid antagonists during pregnancy and the risk of birth defects," N Engl J Med 343, 1608-1614.
Kelly et al, Unmetabolized folic acid in serum: acute studies in subjects consuming fortified food and supplements, Am J Clin Nutr, 1997; 65: 1790-1795.
Mellander et al., Secretory Antibodies in IgA-Deficient and Immunosuppressed Individuals, Journal of Clinical Immunology, vol. 6, No. 4, 1986, pp. 284-291. (Year: 1986).
MRC Vitamin Study Research Group. (1991) "Prevention of neural tube defects: Results of the Medical Research Council Vitamin Study." Lancet 338, 131-137.
Onusic, "Unmetabolized Folic Acid in the Cord Blood of Most Infants: Implications for Future Health, Advances in Nutrition," vol. 7, Issue 1, Jan. 2016: 45A, 2 pages.
Papakostas, GI et al., "L-Methylfolate As Adjunctive Therapy For SSRI-Resistant Major Depression: Results Of Two Randomized, Double-Blind, Parallel-Sequential Trials", Am J Psychiatry, (20121200), vol. 169, pp. 1267-1274, XP055448554, 2012.

(Continued)

*Primary Examiner* — Gary Counts
(74) *Attorney, Agent, or Firm* — Riverside Law LLP

(57) ABSTRACT

Provided are methods, compositions and kits to detect anti-folic acid antibodies in a sample, which are useful for identifying risk of pathologies associated with increased or decreased levels of anti-folic acid antibodies including infertility, folate responsive birth defects, folate responsive blood disorders, heart and vascular diseases, neurological disorders, neurodegenerative diseases and cancers.

6 Claims, 10 Drawing Sheets

(56) References Cited

OTHER PUBLICATIONS

Pfeiffer et al., "Unmetabolized folic acid is detected in nearly all serum samples from US children, adolescents and adults," J Nutr. Mar. 2015; 145(3): 520-31.
Seller (1995) "Neural tube defects, chromosome abnormalities and multiple closure sites for the human neural tube," Clin Dysmorphol 4, 202-207.
SIGMA-Aldrich, Product Information: Monoclonal Anti-Folic Acid Clone VP-52, (Jun. 12, 2015), pp. 1-2, 2015.
Torzewski et al., Animal Models of C-Reactive Protein, Hindawl Publishing Corporation, Mediators of Inflammation, vol. 2014, Article ID 683598, 2014, pp. 1-7. (Year: 2014).
Van Der Vekiens et al., Human and equine cardiovascular endocrinology: beware to compare, Cardiovascular Endocrinology 2013, vol. 2, No. 4, pp. 67-76 (Year: 2013).
Wallingford et al., (2013) "The continuing challenge of understanding, preventing, and treating neural tube defects," Science 339, 1222002, 14 pages.
Wong, J et al., "Rapid Detection Of Antibodies In Sera Using Multiplexed Self-Assembling Bead Arrays", J Immunol Methods, (Nov. 5, 2010), vol. 350, pp. 1-19, XP026684074, 2010.

\* cited by examiner

|  | FA Abs | | FA Blocking | | IgG | | IgM | |
|---|---|---|---|---|---|---|---|---|
|  | Case (ng/mL) | Ctl (ng/mL) | Case (ng/mL) | Ctl (ng/mL) | Case (ng/mL) | Ctl (ng/mL) | Case (ng/mL) | Ctl (ng/mL) |
| AVG | 346.14 | 541.76 | 0.17 | 0.16 | 153.62 | 162.23 | 43.37 | 20.99 |
| STDEV | 120.78 | 192.44 | 0.10 | 0.02 | 152.55 | 59.20 | 39.76 | 5.92 |

Figure 9

| COREL | FA Abs | | FA Blocking | | IgG | | IgM | |
|---|---|---|---|---|---|---|---|---|
| | Case | Ctl | Case | Ctl | Case | Ctl | Case | Ctl |
| All | 0.00 | -0.31 | -0.08 | -0.38 | -0.01 | -0.18 | -0.11 | -0.16 |
| F | 0.01 | -0.30 | -0.12 | -0.38 | 0.00 | -0.37 | -0.08 | -0.42 |
| M | -0.05 | -0.31 | -0.19 | -0.28 | -0.01 | 0.21 | -0.02 | 0.02 |

Figure 10

METHODS OF DETECTING ANTI-FOLIC ACID ANTIBODIES AND USES THEREOF

CROSS-REFERENCE TO RELATED APPLICATIONS

This application is a divisional of U.S. patent application Ser. No. 16/310,059, filed Dec. 14, 2018, which is the U.S. national phase application filed under 35 U.S.C. § 371 claiming benefit to International Patent Application No. PCT/US2017/037404, filed on Jun. 14, 2017, which is entitled to priority under 35 U.S.C. § 119(e) to U.S. provisional application No. 62/349,960, filed Jun. 14, 2016, the disclosures of which are incorporated herein by reference in their entirety.

STATEMENT REGARDING FEDERALLY SPONSORED RESEARCH OR DEVELOPMENT

This invention was made with government support under P01 HD067244 awarded by the National Institutes of Health. The government has certain rights in the invention.

BACKGROUND OF THE INVENTION

Neural tube defects, which include spina bifida, anencephaly, craniorachischisis and encephalocele, occur in approximately 1 per 1200 births in the United States. Additionally, women who have one fetus with this complication are at increased risk in subsequent pregnancies (Cragan et al. (1995) MMWR CDC Surveill Summ 44, 1-13). There are multiple known causes of neural tube defects including drugs, especially antifolate (Hernandez-Diaz et al. (2000), N Engl J Med 343, 1608-1614) and antiepileptic (Dansky et al. (1992) Neurology 42, 32-42) agents, chromosomal abnormalities (Seller (1995) Clin Dysmorphol 4, 202-207), and environmental (Finnell et al. (2000) Ann N Y Acad Sci. 919, 261-277) and genetic factors (De Marco et al. (2000) Am J Med Genet 95, 216-223; Wallingford et al., (2013) Science 339, 1222002). Although periconceptional folic acid supplementation reduces the occurrence and recurrence of neural tube defects by up to 70 percent (Czeizel A. E. and Dudas I. (1992) N Engl J Med 327, 1832-1835; MRC Vitamin Study Research Group. (1991) Lancet 338, 131-137), most women who are pregnant with a fetus with this complication do not have clinical folate deficiency (Giles, C. (1966) J Clin Path 19, 1-11). Though some polymorphisms for folate-pathway enzymes (Christensen et al. (1999) Am J Med Genet 84, 151-157) have been identified, they cannot account for the 70 percent decrease in the incidence of this birth defect with folate supplementation.

Although folic acid supplementation has been shown to reduce the risk of birth defects, specifically, neural tube and conotruncal heart defects, there may be risks associated with consuming synthetic folic acid versus naturally occurring forms of folate. Recent CDC reports indicate that unmetabolized folic acid is detected in nearly all serum samples from US children, adolescents, and adults.

Therefore, there is a need in the art for compositions and methods of identifying subjects for which consumption of synthetic folic acid may pose a health risk. The current invention satisfies this need.

SUMMARY OF THE INVENTION

In one embodiment, the invention relates to a device for detecting anti-folic acid antibodies comprising: a folic acid component and a substrate, wherein the folic acid component is attached to the substrate.

In one embodiment, the folic acid component comprises folic acid or a fragment thereof. In one embodiment, the folic acid component comprises one or more of an analog, a substituted version, a derivative, a fused combination or a salt of folic acid.

In one embodiment, the folic acid component is a folic acid protein conjugate. In one embodiment, the folic acid protein conjugate comprises folic acid, or a fragment thereof, conjugated to keyhole limpet hemocyanin (KLH). In one embodiment, the folic acid protein conjugate comprises folic acid conjugated to biotin.

In one embodiment, the substrate is coated with streptavidin. In one embodiment, the substrate is a bead. In one embodiment, the substrate is a well of a microtiter plate.

In one embodiment, the invention relates to a method of detecting an anti-folic acid antibody in a sample, comprising the steps of a) obtaining a sample; b) contacting the sample with a component that binds to an anti-folic acid antibody; and c) detecting binding between the anti-folic acid antibody and the component. In one embodiment, the component comprises folic acid or a fragment thereof.

In one embodiment, the method of detecting the binding comprises the steps of a) contacting a complex formed by the binding of the anti-folic acid antibody to the component with a labeled biomolecule capable of specifically binding to the complex, and b) detecting a signal from the labeled biomolecule.

In one embodiment, the labeled biomolecule is a labeled immunoglobulin antibody that binds anti-folic acid antibodies. In one embodiment, a labeled immunoglobulin antibody is a labeled IgG, a labeled IgA or a labeled IgM immunoglobulin antibody. In one embodiment, the immunoglobulin antibody is labeled with a fluorescent dye, Digoxigenin (DIG), anti-Digoxigenin, alkaline phosphatase, peroxidase, streptavidin, avidin, or biotin.

In one embodiment, the invention relates to a method of diagnosing a subject with a pathology associated with increased or decreased levels of anti-folic acid antibodies or identifying a subject at risk of developing a pathology associated with increased or decreased levels of anti-folic acid antibodies comprising the steps of a) obtaining a sample of the subject; b) detecting an increased or decreased level of anti-folic acid antibodies in the sample as compared to a comparator control; and c) diagnosing the subject as having a pathology associated with increased or decreased levels of anti-folic acid antibodies or at risk of developing a pathology associated with increased or decreased levels of anti-folic acid antibodies.

In one embodiment, a pathology associated with increased levels of anti-folic acid antibodies is selected from the group consisting of infertility, a folate responsive blood disorder, a folate-associated cancer risk, a heart or vascular disease, a folate-associated neurological disorder, a folate-associated neurodegenerative disease, and a pathology associated with bone development and maintenance.

In one embodiment, a pathology associated with decreased levels of anti-folic acid antibodies is depression that is not responsive to SSRIs.

In one embodiment, the sample is a serum sample.

In one embodiment, the invention relates to a method of diagnosing an infant or unborn child with a pathology associated with increased levels of anti-folic acid antibodies or identifying an infant or unborn child at risk of developing a pathology associated with increased levels of anti-folic acid antibodies comprising the steps of a) obtaining a sample; b) detecting an increased level of anti-folic acid antibodies in the sample as compared to a comparator control; and c) diagnosing the infant as having a pathology associated with increased levels of anti-folic acid antibodies or at risk of developing a pathology associated with increased levels of anti-folic acid antibodies.

In one embodiment, the sample is a serum sample of the infant or unborn child.

In one embodiment, the sample is a maternal serum sample.

In one embodiment, the pathology associated with increased levels of anti-folic acid antibodies is a folate responsive birth defect.

In one embodiment, the folate responsive birth defect is selected from the group consisting of: neural tube defects, heart defects, outflow track defects, septal defects, patent ductus arteriosus, craniofacial defects, gastrointestinal defects, ocular defects, and limb abnormalities.

In one embodiment, the folate responsive birth defect is one or more of cerebral folate deficiency and hereditary folate malabsorption syndrome.

In one embodiment, the invention relates to a method of treating or preventing a pathology associated with increased levels of anti-folic acid antibodies comprising administering a folic acid alternative to a subject identified as having anti-folic acid antibodies present in a sample from the subject.

In one embodiment, the folic acid alternative is one of naturally occurring folate and 5-methyltetrahydrofolate (5MTHF).

In one embodiment, the pathology associated with increased levels of anti-folic acid antibodies is selected from the group consisting of infertility, a folate responsive blood disorder, a folate-associated cancer risk, a heart or vascular disease, a folate-associated neurological disorder, a folate-associated neurodegenerative disease, and a pathology associated with bone development and maintenance.

In one embodiment, the invention relates to a method of treating or preventing a pathology associated with decreased levels of anti-folic acid antibodies comprising administering a folic acid inhibitor to a subject identified as having decreased levels of anti-folic acid antibodies present in a sample from the subject.

In one embodiment, the folic acid inhibitor is an anti-folic acid antibody.

In one embodiment, the pathology associated with decreased levels of anti-folic acid antibodies is depression that is not responsive to SSRIs.

In one embodiment, the invention relates to a method of treating or preventing a pathology associated with increased levels of anti-folic acid antibodies in an infant, wherein anti-folic acid antibodies have been identified in a maternal sample, comprising administering to the infant a folic acid based treatment.

In one embodiment, the invention relates to a kit to detect anti-folic acid antibodies in a sample comprising a device for detecting anti-folic acid antibodies comprising: a folic acid component and a substrate, wherein the folic acid component is attached to the substrate. In one embodiment, the kit further comprises a labeled biomolecule.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 9 depicts the results of an exemplary experimental analysis of IgG anti-folic (FA) acid antibodies (Abs) and blocking, IgG, or IgM autoantibodies to FOLR1 in serum of major depressive disorder (MDD) cases and controls.

FIG. 10 depicts the results of an exemplary experimental analysis of correlations between immunologic measurements and age in cases and controls.

DETAILED DESCRIPTION

Figure 1:
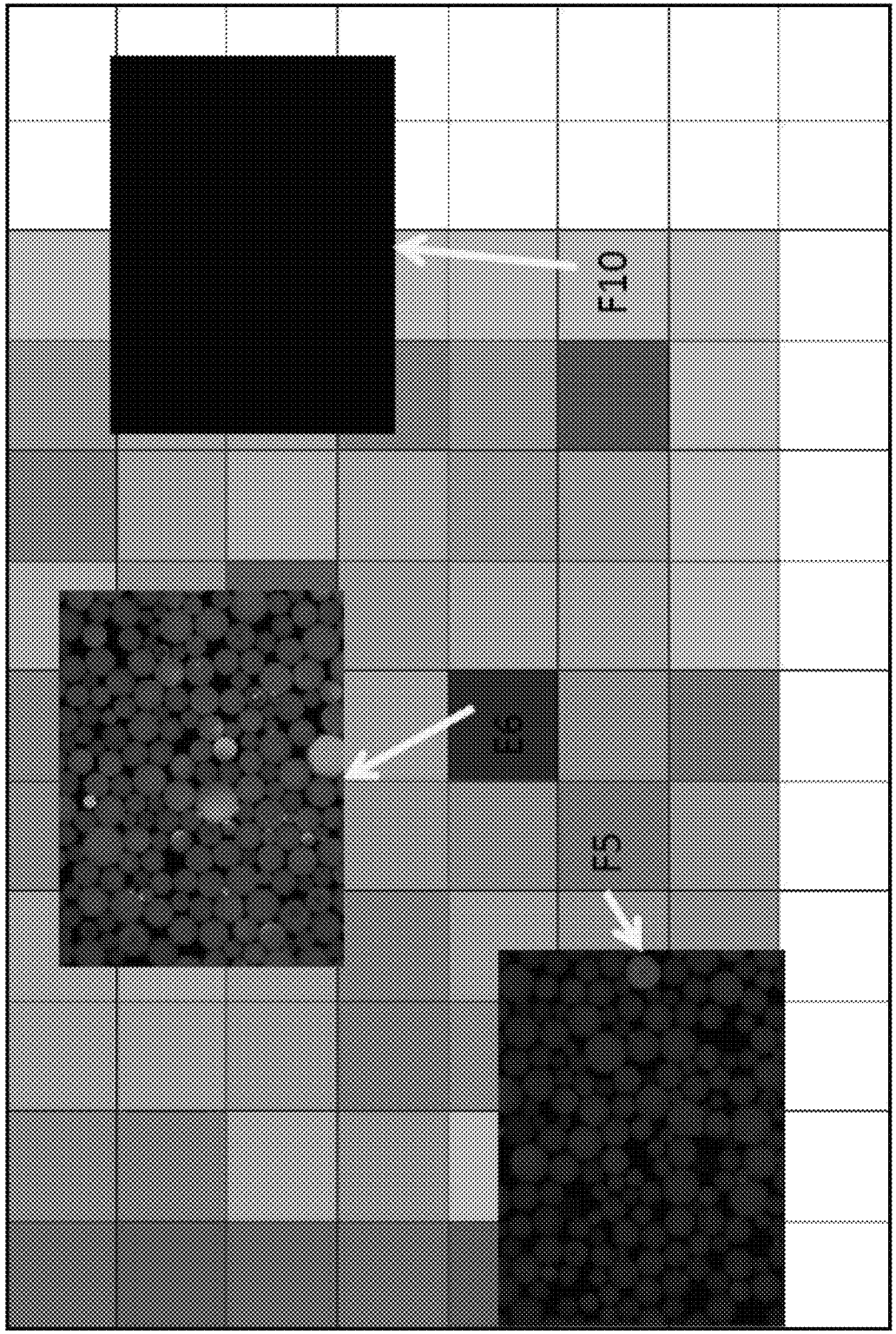
FIG. 1 depicts a heat map of IgG binding to FA-beads in control samples. FA is covalently linked to epoxide resin (54.4 μm±4.9). Seventy control serum samples were contacted with FA-beads in a 96-well plate. Blue squares represent wells containing a test sample. Shading of the blue squared indicates the level of IgG binding in the sample tested (light represents low IgG binding and dark represents high IgG binding).

The present invention is directed to methods, compositions and kits to detect antibodies to folic acid (hereinafter referred to as "anti-folic acid antibodies") in a sample. In one embodiment, the method is useful for detecting anti-folic acid antibodies in a serum sample from a subject. In one embodiment, detecting anti-folic acid antibodies in a serum sample from a subject is useful for identifying risk of a pathology associated with increased or decreased levels of anti-folic acid antibodies in the subject.

In certain embodiments, the invention provides methods, compositions, and kits for identifying risk of a pathology associated with increased or decreased levels of anti-folic acid antibodies in a subject. In certain embodiments, the invention provides methods, compositions, and kits for assessing the risk of developing a pathology associated with increased levels of anti-folic acid antibodies in a fetus of a subject. In one embodiment, the method of the invention relates to detecting anti-folic acid antibodies by contacting a sample with a substrate coated with folic acid and detecting anti-folic acid antibodies bound to the substrate. The invention also relates to compositions and kits useful for performing the method of the invention. In one embodiment, the kit comprises: (a) folic acid or a folic acid protein conjugate and (b) one or more labeled biomolecules.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The phrase "biological sample" is used herein in its broadest sense. A sample may be of any biological tissue or fluid from which biomarkers of the present invention may be assayed. Examples of such samples include but are not limited to blood, lymph, urine, gynecological fluids, biopsies, amniotic fluid and smears. Samples that are liquid in nature are referred to herein as "bodily fluids." Body samples may be obtained from a patient by a variety of techniques including, for example, by scraping or swabbing an area or by using a needle to aspirate bodily fluids. Methods for collecting various body samples are well known in the art. Frequently, a sample will be a "clinical sample," i.e., a sample derived from a patient. Such samples include, but are not limited to, bodily fluids which may or may not contain cells, e.g., blood (e.g., whole blood, serum or plasma), urine, saliva, tissue or fine needle biopsy samples, and archival samples with known diagnosis, treatment and/or outcome history. Biological or body samples may also include sections of tissues such as frozen sections taken for histological purposes. The sample also encompasses any material derived by processing a biological or body sample. Derived materials include, but are not limited to, cells (or their progeny) isolated from the sample, proteins or nucleic acid molecules extracted from the sample. Processing of a biological or body sample may involve one or more of: filtration, distillation, extraction, concentration, inactivation of interfering components, addition of reagents, and the like.

The term "comparator control," as used herein, relates to a level of expression or activity which may be determined at the same time as the test sample, e.g. by using a sample previously collected and stored from a subject who is known to not have antibodies to folic acid.

A "disease" is a state of health of an animal or person wherein the subject cannot maintain homeostasis, and wherein if the disease is not ameliorated then the subject's health continues to deteriorate. In contrast, a "disorder" in a test subject is a state of health in which the subject is able to maintain homeostasis, but in which their state of health is less favorable than it would be in the absence of the disorder. Left untreated, a disorder does not necessarily cause a further decrease in the subject's state of health.

A disease or disorder is "alleviated" if the severity of a sign or symptom of the disease, or disorder, the frequency with which such a sign or symptom is experienced by a patient, or both, is reduced.

As used herein, the term "diagnosis" refers to the determination of the presence of a disease or disorder, such as a bacterial infection. In some embodiments of the present invention, methods for making a diagnosis are provided which permit determination of the presence of a disease or disorder, such as bacterial infection.

The terms "effective amount" and "pharmaceutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation.

As used herein "endogenous" refers to any material from or produced inside the organism, cell, tissue or system.

As used herein, the term "exogenous" refers to any material introduced from or produced outside the organism, cell, tissue or system.

As used herein, an "immunoassay" refers to a biochemical test that measures the presence or concentration of a substance in a sample, such as a biological sample, using the reaction of an antibody to its cognate antigen.

"Instructional material," as that term is used herein, includes a publication, a recording, a diagram, or any other medium of expression which can be used to communicate the usefulness of the composition of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin).

The "level" of one or more biomarkers means the absolute or relative amount or concentration of the biomarker in the sample.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

The terms "normal" and "healthy" are used herein interchangeably. They include an individual or group of individuals who do not have a folate associated pathology and who have not shown any signs or symptoms of a folate acid associated pathology. The term "normal" is also used herein to qualify a sample (e.g., a blood sample) obtained from a healthy individual.

"Naturally-occurring" as applied to an object refers to the fact that the object can be found in nature. For example, naturally occurring folate is a form of folate that can be isolated from a source in nature and which has not been intentionally modified by man.

The term "risk stratification," according to the invention, comprises finding patients, particularly those having anti-folic acid antibodies or infants of those having anti-folic acid antibodies, for the purpose of diagnosis and therapy/treatment of a pathology associated with increased or decreased levels of anti-folic acid antibodies, with the goal of allowing as advantageous a course of the pathology associated with increased or decreased levels of anti-folic acid antibodies as possible.

"Sample" or "biological sample" as used herein means a biological material isolated from an individual. The biological sample may contain any biological material suitable for detecting the desired anti-folic acid antibodies, and may comprise cellular and/or non-cellular material obtained from the individual. One example of a biological sample is a whole blood sample. Another example of a biological sample is a serum sample.

By the term "specifically binds," as used herein, is meant a molecule, such as an antibody, which recognizes and binds to another molecule or feature, but does not substantially recognize or bind other molecules or features in a sample.

"Standard control value" as used herein refers to a predetermined amount of fluorescence from a labeled biomolecule that is not attributable to specific binding. The standard control value is suitable for the use of a method of the present invention, in order for comparing the level of fluorescence from specific binding of a labeled biomolecule to an anti-folic acid antibody that is present in a sample. An established sample serving as a standard control provides a predetermined amount of anti-folic acid antibody.

As used herein, the term "subject" refers to a human or another mammal (e.g., primate, dog, cat, goat, horse, pig, mouse, rat, rabbit, and the like). In many embodiments of the present invention, the subject is a human being. In such embodiments, the subject is often referred to as an "individual" or a "patient." The terms "individual" and "patient" do not denote a particular age.

The term "solid support," "support," and "substrate" as used herein are used interchangeably and refer to a material or group of materials having a rigid or semi-rigid surface or surfaces. In one embodiment it may be desirable to physically separate regions with, for example, wells, raised regions, pins, etched trenches, or the like. According to other embodiments, the substrate(s) will take the form of beads, resins, gels, microspheres, or other geometric configurations. See U.S. Pat. No. 5,744,305 for exemplary substrates.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based on the unexpected detection of anti-folic acid antibodies in serum. Therefore, in various embodiments, the present invention relates to detection of the presence of anti-folic acid antibodies in a biological sample. In one aspect, the invention provides compositions and methods for detecting the presence or amount of antibodies to folic acid in a biological sample.

In certain aspects, the invention relates to diagnosing a pathology associated with increased or decreased levels of anti-folic acid antibodies or identifying an increased risk for one or more pathology associated with increased or decreased levels of anti-folic acid antibodies by detecting the presence or amount of anti-folic acid antibodies in a biological sample. In one aspect, the invention provides compositions and methods for detecting the presence or amount of antibodies to folic acid in a biological sample of a subject at risk for one or more a pathology associated with increased or decreased levels of anti-folic acid antibodies.

In one embodiment, the sample is a biological sample of a subject whose fetus, unborn child, or unconceived child is at risk for one or more a pathology associated with increased or decreased levels of anti-folic acid antibodies. For example, in certain embodiments, the sample is a biological sample of a subject who is pregnant or trying to become pregnant. Therefore, in one embodiment, the invention provides compositions and methods for detecting the presence of antibodies to folic acid in a maternal sample. In one embodiment, the invention provides compositions and methods for detecting the presence of anti-folic acid antibodies in a sample from a subject undergoing fertility treatments. In one embodiment, the invention provides compositions and methods for detecting the presence of anti-folic acid antibodies in a sample from a subject who is taking a pre-natal supplement.

In one embodiment, the sample is a biological sample of a subject having or at risk for a neurological disorder or pathology. In one embodiment, a neurological disorder or pathology is major depressive disorder (MDD) that is not responsive to SSRIs.

In one embodiment, the invention relates to an immunoassay device that can be used for detecting an anti-folic acid antibody in a sample, and an immunoassay method using the same. In various embodiments, the immunoassay device can be used to detect an increased or decreased level of anti-folic acid antibodies in a sample as compared to a comparator control.

In another embodiment, the system of the invention may comprise any method known in the art to effectively detect an anti-folic acid antibody in a sample. Suitable methods include, but are not limited to, immunoassays, enzyme assays, mass spectrometry, biosensors, and chromatography. Thus, the system of the invention includes the use of any type of instrumentality to detect an anti-folic acid antibody.

In various embodiments, the invention relates to methods of treating or preventing a pathology associated with increased levels of anti-folic acid antibodies in a subject having an increased level of anti-folic acid antibodies. A pathology associated with increased levels of anti-folic acid antibodies may be one of infertility, a folate responsive birth defect (e.g. neural tube defects, heart defects including outflow track defects, septal defects and patent ductus arteriosus, craniofacial defects including facial clefts, cleft lip and cleft palate, gastrointestinal defects including omphalocele and gastroschisis, ocular defects including anophthalmia and microphthalmia, and limb abnormalities), a folate responsive blood disorder (e.g. megaloblastic anemia and pancytopenia), folate-associated cancer risk (e.g. risk of colorectal, breast, lung, esophageal, pancreatic, liver, head and neck, acute lymphoblastic leukemia (ALL), endometrial, and ovarian cancer), heart and vascular disease (e.g. coronary heart disease, stroke, peripheral artery disease, atherosclerosis), a folate-associated neurological disorder (e.g. autism, depression, and anxiety), a folate-associated neurodegenerative disease (e.g. Alzheimer's), and a pathology associated with bone development or maintenance (e.g. low bone mineral density and osteoporosis). In one embodiment, a folate-associated pathology is cerebral folate deficiency syndrome. In one embodiment, a folate-associated pathology is hereditary folate malabsorption syndrome.

While autoantibodies to folate receptor are reported as associated with diseases such as major depressive disorder, the invention is based in part on the observation that antibodies to folic acid are strongly protective, with increased levels of antibodies associated with a decrease in risk. Therefore, in certain aspects, the invention relates to detecting a neurological disorder or pathology or diagnosing an increased risk for one or more neurological disorder or pathologies by detecting a decreased level of anti-folic acid antibodies in a biological sample as compared to a comparator control. Therefore, in one embodiment, the invention provides compositions and methods for detecting the presence of antibodies to folic acid in a sample from a subject diagnosed as having or at risk of having a one or more neurological disorder or pathologies. In one embodiment, a neurological disorder or pathology is major depressive disorder (MDD), dysthymia, subsyndromal depression, postpartum depression, bipolar depression, depressive psychosis, dysphoria, mourning syndrome, postoperative depression, premenstrual dysphoric disorder, pseudodementia, puerperal depression, and seasonal affective disorder. In one embodiment, the subject has failed to respond to the use of an SSRI (i.e. the depression is not responsive to SSRIs).

In various embodiments, the invention relates to methods of treating or preventing a neurological disorder or pathology through administering a folic acid inhibitor or antagonist to a subject identified as having low levels of folic acid antibodies. In one embodiment, a folic acid inhibitor or antagonist is a folic acid antibody.

Methods

In one embodiment, the invention is a method of identifying or quantifying the amount of anti-folic acid antibodies in a subject. In one embodiment, the method comprises determining the presence or amount of anti-folic acid antibodies in a sample as compared to a comparator control. The methods of the invention can be used to detect, diagnose or treat a subject having or at risk of developing of a pathology associated with increased or decreased levels of anti-folic acid antibodies.

In one embodiment, the method relates to detecting the presence of or increased levels of anti-folic acid antibodies in a subject as compared to a comparator control. In one embodiment, the invention is a method for diagnosing a pathology associated with increased levels of anti-folic acid antibodies or identifying risk of the development of a pathology associated with increased levels of anti-folic acid antibodies in a subject based on the detection of increased levels of anti-folic acid antibodies. In one embodiment, the invention provides a method for diagnosing a pathology associated with increased levels of anti-folic acid antibodies or identifying risk of the development of a pathology associated with increased levels of anti-folic acid antibodies in a fetus, unborn child, or unconceived child of a subject based on the detection of increased levels of anti-folic acid in a sample of the subject.

In one embodiment, the method relates to detecting the presence of or decreased levels of anti-folic acid antibodies in a subject as compared to a comparator control. In one embodiment, the invention is a method for diagnosing a pathology associated with decreased levels of anti-folic acid antibodies or identifying risk of the development of a pathology associated with decreased levels of anti-folic acid antibodies in a subject based on the detection of decreased levels of anti-folic acid antibodies.

The present invention features methods for identifying subjects having a pathology associated with increased or decreased levels of anti-folic acid antibodies, or who are at risk of developing a pathology associated with increased or decreased levels of anti-folic acid antibodies, including those subjects who are asymptomatic or only exhibit non-specific indicators of a folate-associated pathology by detection or quantification of anti-folic acid antibodies, as disclosed herein.

The detection of anti-folic acid antibodies is also useful for monitoring subjects undergoing treatments and therapies for a pathology associated with increased or decreased levels of anti-folic acid antibodies, and for selecting or modifying therapies and treatments that would be efficacious in subjects having a pathology associated with increased or decreased levels of anti-folic acid antibodies, wherein selection and use of such treatments and therapies slow the progression of the pathology associated with increased or decreased levels of anti-folic acid antibodies, or prevent their onset.

The invention provides improved methods for the diagnosis and prognosis of pathologies associated with increased or decreased levels of anti-folic acid antibodies. The risk of developing a pathology associated with increased or decreased levels of anti-folic acid antibodies can be assessed by measuring the level of anti-folic acid antibodies in a biological sample of the subject, and comparing the measured values to comparator values, reference values, or index values. Such a comparison can be undertaken with mathematical algorithms or formula in order to combine information from results of multiple individual biomarkers and other parameters into a single measurement or index. Subjects identified as having an increased risk of a pathology associated with increased or decreased levels of anti-folic acid antibodies can optionally be selected to receive treatment regimens, such as administration of prophylactic or therapeutic compounds to prevent, treat or delay the onset of the pathology.

Identifying a subject before they develop a pathology associated with increased or decreased levels of anti-folic acid antibodies enables the selection and initiation of various therapeutic interventions or treatment regimens in order to delay, reduce or prevent that subject's conversion to a disease state. Monitoring the levels of anti-folic acid antibody also allows for the course of treatment of a pathology associated with increased or decreased levels of anti-folic acid antibodies to be monitored. For example, a sample can be provided from a subject undergoing treatment regimens or therapeutic interventions, e.g., drug treatments, for a pathology associated with increased or decreased levels of anti-folic acid antibodies. Samples can be obtained from the subject at various time points before, during, or after treatment.

Data concerning the presence or level of anti-folic acid antibody can also be combined or correlated with other data or test results, such as, without limitation, measurements of clinical parameters or other algorithms for a pathology associated with increased or decreased levels of anti-folic acid antibodies. Other data includes gender, age, ethnicity, height, weight, diet, smoking status, exercise level, sleeping habits, and the like. The data can also comprise subject information such as medical history and any relevant family history.

The present invention also provides methods for identifying agents for treating a pathology associated with increased or decreased levels of anti-folic acid antibodies that are appropriate or otherwise customized for a specific subject. In this regard, a test sample from a subject, exposed to a therapeutic agent or a drug, can be taken and the level of anti-folic acid antibody can be determined. The level of anti-folic acid antibody can be compared to a sample derived from the subject before and after treatment, or can be compared to samples derived from one or more subjects who have shown improvements in risk factors as a result of such treatment or exposure.

In various embodiments, the level of anti-folic acid antibody in the biological sample of the subject is compared with the level of anti-folic acid antibody in a comparator. Non-limiting examples of comparators include, but are not limited to, a negative control, a positive control, standard control, standard value, an expected normal background value of the subject, a historical normal background value of the subject, a reference standard, a reference level, an expected normal background value of a population that the subject is a member of, or a historical normal background value of a population that the subject is a member of.

In another embodiment, the invention is a method of monitoring the progression of a pathology associated with increased or decreased levels of anti-folic acid antibodies in a subject by assessing the level of one or more of the markers of the invention in a biological sample of the subject.

In one embodiment, a pathology associated with decreased levels of anti-folic acid antibodies is depression that is not responsive to SSRIs. Thus, the present invention encompasses methods for identifying subjects having depression that is not responsive to SSRI, or who are at risk of developing depression that is not responsive to SSRI. For example, in one embodiment, the method comprises detecting the level of anti-folic acid antibody in a subject having depression, suspected to have depression, or at risk for developing depression. In one embodiment, the method comprises diagnosing a subject having a low level of anti-folic acid antibody, as compared to a control, as having depression that is non-responsive to SSRI treatment. In certain embodiments, the method provides for the detection of decreased levels of anti-folic acid antibody in a sample from a subject as compared to a comparator control to determine or modify a treatment regimen being administered to the subject.

In certain embodiments, the method comprises administering a treatment regimen to a subject diagnosed has having a pathology associated with decreased levels of anti-folic acid antibodies. In one embodiment, the subject is diagnosed as having depression that is non-responsive to SSRI treatment. In one embodiment, a treatment regimen comprises administering a folic acid inhibitor or folic acid antagonist to the subject. In one embodiment, a folic acid inhibitor comprises an anti-folic acid antibody. In one embodiment, the folic acid inhibitor is administered in combination with an SSRI depression treatment regimen (e.g., a combination of an anti-folic acid antibody and an SSRI such as Citalopram, Escitalopram, Fluoxetine, Paroxetine, Sertraline, or Vilazodone). In one embodiment, a treatment regimen comprises administering a non-SSRI depression treatment regimen (e.g., a combination of a folic acid inhibitor and a non-SSRI treatment such as, but not limited to, a serotonin-norepinephrine reuptake inhibitor, a monoamine oxidase inhibitor, a non-SSRI antidepressant, or another medication for the treatment of depression). In one embodiment, a treatment regimen comprises administering a folic acid inhibitor to the subject in combination with a non-SSRI depression treatment regimen.

In various embodiments, the subject is a human subject, and may be of any race, sex and age. In various embodiments, the test sample is a biological sample (e.g., fluid, tissue, cell, cellular component, etc.) of the subject. In some embodiments, the biological sample is blood, plasma, saliva, sweat, stool, vaginal fluid, amniotic fluid, or urine. In one embodiment, the biological sample is serum.

A biological sample can be obtained by appropriate methods, such as, by way of examples, blood draw, fluid draw, or biopsy. A biological sample can be used as the test sample; alternatively, a biological sample can be processed to enhance access to the antibodies and the processed biological sample can then be used as the test sample.

The methods of detecting an anti-folic acid antibody may be carried out using any assay or methodology known in the art. In various embodiments of the invention, methods of measuring an anti-folic acid antibody in a biological sample include, but are not limited to, an immunochromatography assay, an immunodot assay, a Luminex assay, an ELISA assay, an ELISPOT assay, a protein microarray assay, a ligand-receptor binding assay, an immunostaining assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

In certain embodiments, the method comprises the steps of contacting a sample with a component that binds to an anti-folic acid antibody and detecting the binding of the anti-folic acid antibody to the component. In certain embodiments, the component comprises folic acid, or fragment thereof. In certain embodiments, the binding of the anti-folic acid antibody to the component forms a complex, where detection of the complex is used to detect that an anti-folic acid antibody of the sample has bound to the component. For example, the complex can be contacted with a labeled molecule that is capable of binding to the complex or portion thereof. In certain embodiments, detection of the complex is accomplished by detecting the labeled molecule bound to the complex.

In certain embodiments, the method comprises the steps of contacting a sample with a folic acid-coated substrate and detecting the binding of anti-folic acid antibodies present in the sample to the folic acid. In one embodiment, the method of detection comprises contacting an anti-folic acid antibody:folic acid complex with a labeled biomolecule and measuring the detectable signal from the labeled biomolecule.

In one embodiment, the method comprises contacting a sample with beads wherein folic acid is attached to the surface of the bead. In one embodiment, the folic acid is attached to the surface of the bead through a biotin:streptavidin interaction. In one embodiment, a bead is an epoxide resin bead. In one embodiment, a bead is a magnetic bead. In one embodiment, the resin size is selected to be compatible with a preferred detection method. In one embodiment, the resin size is about 50 and is selected to be compatible with flow cytometry and microscopy.

In one embodiment, the method comprises placing an aliquot of a sample in a well of a microtiter plate, wherein the well contains a folic acid protein conjugate. In one embodiment, a microtiter plate is a cell culture plate. In one embodiment, the well contains folic acid conjugated to keyhole limpet hemocyanin (KLH).

An anti-folic acid antibody may specifically bind to a fragment of folic acid. Therefore, in one embodiment, the method of the invention comprises a method for identifying the specificity of an anti-folic acid antibody in a sample. For example, in various embodiments, a sample is applied to one or more fragments of folic acid, analogs thereof, fused combinations thereof, substituted versions thereof, derivatives thereof or salts thereof, and binding to the one or more fragments, analogs, fused combinations, substituted versions, derivatives or salts are detected to determine the specificity of an anti-folic acid antibody in a sample. In one embodiment, a sample is a blood or serum sample.

In one embodiment, the labeled biomolecule is a labeled immunoglobulin antibody that binds an anti-folic acid antibody:folic acid complex. In one embodiment, a labeled immunoglobulin antibody is one of anti-human IgG, anti-human IgM, anti-mouse IgG and anti-mouse IgM. In one embodiment, the labeled IgG immunoglobulin antibody is a labeled IgG1, labeled IgG2, labeled IgG3, or labeled IgG4 immunoglobulin antibody. In one embodiment, the label is selected from the group consisting of fluorescent dye, a cyanine dye, Digoxigenin, anti-Digoxigenin, alkaline phosphatase, peroxidase, avidin, streptavidin and biotin. In one embodiment, a cyanine dye is one of Cy®3 and Cy® 5.

In various embodiments, the method further comprises such washing steps as are necessary to remove unbound molecules (e.g. proteins, peptides, antibodies and nucleic acid molecules) and to remove solutions that may interfere with one or more of the binding step and the detection steps.

In various embodiments of the method of the invention, the presence of, or increased levels of, anti-folic acid antibodies is determined when the labeled biomolecule is detected at a level that is increased by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, in the biological sample when compared with a comparator control.

In various embodiments of the method of the invention, decreased levels of anti-folic acid antibodies is determined when the labeled biomolecule is detected at a level that is decreased by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, in the biological sample when compared with a comparator control.

In various embodiments of the methods of the invention, the presence of, or increased levels of, anti-folic acid antibodies is determined when the labeled biomolecule is detected at a level that is increased by at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 20 fold, at least 25 fold, at least 30 fold, at least 40 fold, at least 50 fold, at least 75 fold, at least 100 fold, at least 200 fold, at least 250 fold, at least 500 fold, or at least 1000 fold, in the biological sample when compared with a comparator control.

In various embodiments of the methods of the invention, decreased levels of anti-folic acid antibodies is determined when the labeled biomolecule is detected at a level that is decreased by at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 20 fold, at least 25 fold, at least 30 fold, at least 40 fold, at least 50 fold, at least 75 fold, at least 100 fold, at least 200 fold, at least 250 fold, at least 500 fold, or at least 1000 fold, in the biological sample when compared with a comparator control.

In one embodiment, the invention is a method of identifying anti-folic acid antibodies in a subject. In various embodiments, the method includes distinguishing between decreased levels of anti-folic acid antibodies and increased levels of anti-folic acid antibodies in subjects.

Comparison of the level of the detectable signal in a sample to be tested with those of controls can be used to identify the presence or level of an anti-folic acid antibody in the sample. In this context, the control or control group is used for purposes of establishing initial cutoffs for the systems and assay of the invention. Therefore, mere detection of an anti-folic acid antibody of the invention without the requirement of comparison to a control group can diagnose a risk of a pathology associated with increased or decreased levels of anti-folic acid antibodies. In this manner, the system according to the present invention may be used for qualitative (yes/no answer); semi-quantitative (−/+/++/+++/++++) or quantitative answer.

Information obtained from the methods of the invention described herein can be used alone, or in combination with other information (e.g., pregnancy status, fertility history, vital signs, blood chemistry, etc.) from a subject or from a biological sample obtained from a subject.

Immunoassays

In one embodiment, the methods of the invention can be performed in the form of various immunoassay formats, which are well known in the art. Immunoassays, in their most simple and direct sense, are binding assays involving binding between antibodies and antigen. Many types and formats of immunoassays are known and all are suitable for detecting the disclosed anti-folic acid antibodies. Examples of immunoassays are enzyme linked immunosorbent assays (ELISAs), enzyme linked immunospot assay (ELISPOT), radioimmunoassays (MA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), fluorescence recovery/localization after photobleaching (FRAP/FLAP), a sandwich assay, a competitive assay, an immunoassay using a biosensor, an immunoprecipitation assay, an agglutination assay, a turbidity assay, a nephlelometric assay, etc.

In general, immunoassays involve contacting a sample suspected of containing a molecule of interest (such as the disclosed anti-folic acid antibodies) with a molecule that can be bound by the antibody, as the case may be, under conditions effective to allow the formation of immunocomplexes. Contacting a sample with the molecule that can be bound by an antibody to the molecule of interest under conditions effective and for a period of time sufficient to allow the formation of immune complexes (primary immune complexes) is generally a matter of simply bringing into contact the molecule and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes (e.g., horseradish peroxidase) that react with colorometric substrates. The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that fluoresce. Typically fluorophores absorb electromagnetic energy at one wavelength and emit electromagnetic energy at a second wavelength.

Luminescence does not require excitation, but produces luminescent emission (glowing) due to enzymatic cleavage (e.g. horseradish peroxidase activity on a luminescent substrate).

There are two main types of immunoassays, homogeneous and heterogeneous. In homogeneous immunoassays, both the immunological reaction between an antigen and an antibody and the detection are carried out in a homogeneous reaction. Heterogeneous immunoassays include at least one separation step, which allows the differentiation of reaction products from unreacted reagents. A variety of immunoassays can be used to detect one or more of the proteins disclosed or incorporated by reference herein.

ELISA is a heterogeneous immunoassay, which can be used in the methods disclosed herein. The assay can be used to detect protein antigens in various formats. In the "sandwich" format the antigen being assayed is held between two different antibodies. In this method, a solid surface is first coated with a solid phase antibody. The test sample, containing the antigen (e.g., a diagnostic protein), or a composition containing the antigen, such as a biological sample from a subject of interest, is then added and the antigen is allowed to react with the bound antibody. Any unbound antigen is washed away. A known amount of enzyme-labeled antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the antigen present in the sample tested. In one embodiment, an ELISA-based assay for use in the method of the invention utilizes folic acid bound to a substrate in place of a first antibody.

ELISA can also be used as a competitive assay. In the competitive assay format, the test sample containing the antigen to be determined is mixed with a precise amount of enzyme-labeled antigen and both compete for binding to an anti-antigen antibody attached to a solid surface. Excess free enzyme-labeled antigen is washed off before the substrate for the enzyme is added. The amount of color intensity resulting from the enzyme-substrate interaction is a measure of the amount of antigen in the sample tested. A heterogeneous immunoassay, such as an ELISA, can be used to detect the anti-folic acid antibodies described herein.

In many immunoassays, detection of antigen is made with the use of antigens specific antibodies as detector molecules. However, immunoassays and the systems and methods of the present invention are not limited to the use of antibodies as detector molecules. Any substance that can bind or capture the antigen within a given sample may be used. Aside from antibodies, suitable substances that can also be used as detector molecules include but are not limited to enzymes, peptides, proteins, and nucleic acids. Further, there are many detection methods known in the art in which the captured antigen may be detected. In some assays, enzyme-linked antibodies produce a color change. In other assays, detection of the captured antigen is made through detecting fluorescent, luminescent, chemiluminescent, or radioactive signals. The system and methods of the current invention is not limited to the particular types of detectable signals produced in an immunoassay.

Biosensors

In one embodiment, the anti-folic acid antibodies of the invention are detected using biosensors, e.g. with sensor systems with amperometric, electrochemical, potentiometric, conductimetric, impedance, magnetic, optical, acoustic or thermal transducers.

Generally, biosensors include a biosensor recognition element which can include proteins, nucleic acids, antibodies, etc. that bind to a particular biomarker and a transducer which converts a molecular signal (i.e. binding of biomarker to recognition element) into an electric or digital signal that can be quantified, displayed, and analyzed. Biosensors may also include a reader device which translates the signal into a user-friendly display of the results. Examples of potential components that comprise an exemplary biosensor are described in Bohunicky et al. (2011, Nanotechnology Science and Applications, 4: 1-10), which is hereby incorporated by reference in its entirety.

A biosensor may incorporate a physical, chemical or biological detection system. In one embodiment, a biosensor is a sensor with a biological recognition system, e.g. based on a nucleic acid, such as an oligonucleotide probe or aptamer, or a protein such as an enzyme, binding protein, receptor protein, transporter protein or antibody. In one embodiment, the biological recognition system may comprise traditional immunoassays described elsewhere herein. In another element, the recognition element (e.g. protein, nucleic acid, antibody, etc.) may be unlabeled and binding of the biomarker to the element is directly observed and converted into a signal by the transducer.

The method for detection of the biomarker in a biosensor may comprise immunological, electrical, thermal, magnetic, optical (e.g. hologram) or acoustic technologies. Using such biosensors, it is possible to detect the target biomarker at the anticipated concentrations found in biological samples.

The biosensor may incorporate detection methods and devices as described herein for detection of the anti-folic acid antibodies. Biosensors may employ electrical (e.g. amperometric, potentiometric, conductimetric, or impedance detection systems), calorimetric (e.g. thermal), magnetic, optical (e.g. hologram, luminescence, fluorescence, colorimetry), or mass change (e.g. piezoelectric, acoustic wave) technologies. In a biosensor according to the invention the level of an anti-folic acid antibody of the invention can be detected by one or more methods selected from: direct, indirect or coupled enzymatic, spectrophotometric, fluorimetric, luminometric, spectrometric, polarimetric and chromatographic techniques. Particularly preferred biosensors comprise a folic acid component used directly or indirectly via a mediator, or using a binding, receptor or transporter protein, coupled to an electrical, optical, acoustic, magnetic or thermal transducer. Using such biosensors, it is possible to detect the level of anti-folic acid antibody at the anticipated concentrations found in biological samples.

Biosensors to detect the anti-folic acid antibody of the invention may include acoustic, surface plasmon resonance, holographic and microengineered sensors. Imprinted recognition elements, thin film transistor technology, magnetic acoustic resonator devices and other novel acousto-electrical systems may be employed in biosensors for detection of the biomarkers of the invention.

Suitably, biosensors for detection of the anti-folic acid antibody of the invention are coupled, i.e. they combine biomolecular recognition with appropriate means to convert detection of the presence, or quantitation, of the anti-folic acid antibody in the sample into a signal. Biosensors can be adapted for "alternate site" diagnostic testing, e.g. in the ward, outpatients' department, surgery, home, field and workplace.

Methods involving detection and/or quantification of the anti-folic acid antibody of the invention can be performed using bench-top instruments, or can be incorporated onto disposable, diagnostic or monitoring platforms that can be used in a non-laboratory environment, e.g. in the physician's office or at the patient's bedside.

Treatments

Identifying a subject before they develop a pathology associated with increased or decreased levels of anti-folic acid antibodies enables the selection and initiation of various therapeutic interventions or treatment regimens in order to delay, reduce or prevent that subject's conversion to a disease state. In one aspect, the invention provides a method of treating or preventing a pathology associated with increased or decreased levels of anti-folic acid antibodies in a subject, wherein the subject has been identified as having increased or decreased levels of anti-folic acid antibodies.

In certain embodiments, the method comprises administering a folic acid alternative to a subject identified as having anti-folic acid antibodies. In another aspect, the invention provides a method of treating or preventing a folic acid related pathology in an unborn child, a fetus or an unconceived child of a subject, wherein the subject has been identified as having anti-folic acid antibodies, comprising administering a folic acid alternative to the subject. In yet another aspect, the invention provides a method of treating or preventing a folic acid related pathology in an infant of a subject, wherein the subject has been identified as having anti-folic acid antibodies, comprising administering folic acid or a folic acid alternative to the infant.

Folic acid alternatives or therapeutic interventions can include dietary modification and dietary supplementation. Exemplary folic acid alternatives includes, but is not limited to, naturally occurring folate and 5-methyltetrahydrofolate (5MTHF).

In one embodiment, a folic acid alternative is administered to a subject at a dosage that is determined based on the age, height, weight and pregnancy status of the subject. In one embodiment, such a dosage is 400-600 mcg of naturally occurring folate. In one embodiment, such a dosage of 5MTHF is 0.4 mg/day total for a non-pregnant woman. In one embodiment, such a dosage of 5MTHF is 0.8 mg/day total for a pregnant woman.

Folic acid based treatments can include folic acid or a folic acid alternative. In one embodiment, folic acid may be administered to an infant who does not have anti-folic acid antibodies when anti-folic acid antibodies were detected in a maternal sample. In one embodiment, a folic acid alternative may be administered to an infant when anti-folic acid antibodies were detected in a maternal sample. In one embodiment, a folic acid alternative may be administered to an infant when anti-folic acid antibodies are detected in a sample from the infant.

In one embodiment, a folic acid based treatment is administered to an infant of a subject at a dosage that is determined based on the age, height and weight of the infant. In various embodiments, an infant is less than 6 months, less than 5 months, less than 4 months, less than 3 months, less than 2 months, less than 1 month, less than 4 weeks, less than 3 weeks, less than 2 weeks, less than 1 week, less than 6 days, less than 5 days, less than 4 days, less than 3 days, less than 2 days, or less than 1 day old. In one embodiment, such a dosage is about 0.1-10 mg/kg/day of 5MTHF. In one embodiment, such a dosage is about 0.25-5 mg/kg/day of 5MTHF. In one embodiment, such a dosage is about 0.5-1 mg/kg/day of 5MTHF.

In one embodiment, a folic acid inhibitor is an anti-folic acid antibody. In one embodiment an anti-folic acid antibody is administered to a subject identified as having decreased levels of anti-folic acid antibodies. For example, in one embodiment, the treatment method relates to providing an anti-folic acid antibody to a subject having depression, wherein the subject has been further identified as having decreased levels of anti-folic acid antibodies. Types of depression that can be treated according to the invention include, but are not limited to, major depressive disorder (MDD), dysthymia, subsyndromal depression, post-partum depression, bipolar depression, depressive psychosis, dysphoria, mourning syndrome, postoperative depression, premenstrual dysphoric disorder, pseudodementia, puerperal depression, and seasonal affective disorder. In one embodiment, the subject has failed to respond to the use of an SSRI (i.e. the depression is not responsive to SSRIs).

In one embodiment, a folic acid inhibitor is administered to a subject in combination with an SSRI treatment. SSRI treatments include, but are not limited to fluoxetine, citalopram, fluvoxamine, sertraline, paroxetine, and escitalopram. In one embodiment, a folic acid alternative treatment is administered to a subject in combination with a non-SSRI treatment. Non-SSRI treatments include, but are not limited to a serotonin-norepinephrine reuptake inhibitor, a monoamine oxidase inhibitor, a non-SSRI antidepressant, and other drugs. Serotonin-norepinephrine reuptake inhibitors include, but are not limited to, duloxetine hydrochloride, venlafaxine, and desvenlafaxine succinate. Monoamine oxidase inhibitors include, but are not limited to, phenelzine sulfate, tranylcypromine sulfate, emsam and moclobemide. Non-SSRI antidepressants include, but are not limited to, doxepin, clomipramine, amitriptyline, maprotiline, desipramine, trimipramine, imipramine, protriptyline hydrochloride, agomelatine, reboxetine, trazodone, mirtazapine, nefazodone and bupropion. Other drugs include, but are not limited to, buspirone, gepirone, tandospirone; risperidone, olanzapine, quetiapine, aripiprazole, ziprasidone, amphetamine, methylphenidate, bromocriptine, cabergoline, pergolide, pramipexole, ropinirole, apomorphine, rotigotine, lithium, pindolol, tryptophan, carbamazepine, sodium valproate, lamotrigine, mifepristone, testosterone, estrogen, progesterone and thyroid medications.

In one embodiment, the method comprises administering a treatment regimen to a subject diagnosed as having depression that is not responsive to SSRIs, wherein the subject has been identified as having decreased levels of anti-folic acid antibodies. In one embodiment, the treatment method is a non-SSRI based treatment method.

In one embodiment, the method relates to providing an alternative treatment regimen or modifying a treatment regimen being administered to a subject, wherein the subject has been identified as having decreased levels of anti-folic acid antibodies. For example, in one embodiment, the method comprises detecting decreased levels of anti-folic acid antibodies in a sample of a subject diagnosed as having depression as compared to a comparator control, wherein the subject has been administered an SSRI-based treatment, diagnosing the subject as having depression that is not responsive to SSRI treatment, and providing an alternative treatment. In one embodiment, the treatment is a non-SSRI treatment.

Devices

The invention provides devices for detecting the presence or level of anti-folic acid antibodies in a sample. In one embodiment, the invention provides a device comprising a folic acid component and a substrate. In one embodiment, a substrate is one of a bead, a microarray or a microtiter plate. Therefore, in one embodiment, a device of the invention comprises a substrate-modified microarray or microtiter plate, comprising a folic acid component for use in an assay of the invention. In one embodiment, a folic acid component is provided bound to a bead. In one embodiment, a bead is a streptavidin coated magnetic bead.

In one embodiment, a folic acid component of a device of the invention comprises folic acid or fragment thereof. In one embodiment, a folic acid component comprises a folic acid protein conjugate. In one embodiment, a folic acid protein conjugate comprises folic acid conjugated to KLH. In alternative embodiments, a protein appropriate for forming a folic acid protein conjugate includes, but is not limited to, BSA and OVA. In one embodiment, the folic acid molecule is conjugated to biotin. In one embodiment, a folic acid molecule conjugated to a protein may further comprise a linker, for example a PEG linker.

In one embodiment, the folic acid component of a device of the invention comprises one or more fragment of folic acid. In one embodiment, the folic acid component comprises one or more analogs of folic acid. In one embodiment, the folic acid component comprises one or more substituted versions of folic acid. In one embodiment, the folic acid component comprises one or more derivatives of folic acid. In one embodiment, the folic acid component comprises one or more fused combination of folic acid.

In one embodiment, the folic acid component is conjugated to KLH. In alternative embodiments, the folic acid component is conjugated to a protein selected from, but not limited to, BSA and OVA. In one embodiment, the folic acid component is conjugated to biotin. In one embodiment, the folic acid component may further comprise a linker, for example a PEG linker.

In one embodiment, the device of the invention can be utilized in a method that takes the form of a laboratory test, for example a type of numbered well plate (e.g., 96 well plate).

In some instances, the device of the invention may take the form of a user-friendly point-of-use or point-of-care platform, for example a lateral flow device, having a sample application region and a readable detection region to indicate the presence or absence of the anti-folic acid antibody or variable levels of the anti-folic acid antibody. In one embodiment, the readable detection region includes a test line and a control line, wherein the test line detects the anti-folic acid antibody.

In one embodiment, the device of the invention can be in the form of a cartridge that can be read by a machine. Preferably, the machine is automated.

Point-of-Use Devices

Point-of-use analytical tests have been developed for the routine identification or monitoring of health-related conditions (such as pregnancy, cancer, endocrine disorders, infectious diseases or drug abuse) using a variety of biological samples (such as urine, serum, plasma, blood, saliva). Some of the point-of-use assays are based on highly specific interactions between specific binding pairs, such as antigen/antibody, hapten/antibody, lectin/carbohydrate, apoprotein/cofactor and biotin/(strept)avidin. In some point-of use devices, assays are performed with test strips in which a specific binding pair member is attached to a mobilizable material (such as a metal sol or beads made of latex or glass) or an immobile substrate (such as glass fibers, cellulose strips or nitrocellulose membranes). Other point-of use devices may comprise optical biosensors, photometric biosensors, electrochemical biosensor, or other types of biosensors. Suitable biosensors in point-of-use devices for performing methods of the invention include "cards" or "chips" with optical or acoustic readers. Biosensors can be configured to allow the data collected to be electronically transmitted to the physician for interpretation and thus can form the basis for e-medicine, where diagnosis and monitoring can be done without the need for the patient to be in proximity to a physician or a clinic.

Detection of an anti-folic acid antibody in a sample can be carried out using a sample capture device, such as a lateral flow device (for example a lateral flow test strip).

The test strips of the present invention include a flow path from an upstream sample application area to a test site. For example, the flow path can be from a sample application area through a mobilization zone to a capture zone. The mobilization zone may contain a mobilizable marker that interacts with an analyte or analyte analog, and the capture zone contains a reagent that binds the analyte or analyte analog to detect the presence of an analyte in the sample.

Examples of migration assay devices, which usually incorporate within them reagents that have been attached to colored labels, thereby permitting visible detection of the assay results without addition of further substances are found, for example, in U.S. Pat. No. 4,770,853 (incorporated herein by reference). There are a number of commercially available lateral-flow type tests and patents disclosing methods for the detection of large analytes (MW greater than 1,000 Daltons) as the analyte flows through multiple zones on a test strip. Examples are found in U.S. Pat. Nos. 5,229,073, 5,591,645; 4,168,146; 4,366,241; 4,855,240; 4,861,711; 5,120,643 (each of which are herein incorporated by reference). Multiple zone lateral flow test strips are disclosed in U.S. Pat. Nos. 5,451,504, 5,451,507, and 5,798, 273 (incorporated by reference herein). U.S. Pat. No. 6,656, 744 (incorporated by reference) discloses a lateral flow test strip in which a label binds to an antibody through a streptavidin-biotin interaction.

Flow-through type assay devices were designed, in part, to obviate the need for incubation and washing steps associated with dipstick assays. Flow-through immunoassay devices involve a capture reagent (such as folic acid, a folic acid protein conjugate or a fragment or chemical analog of folic acid) bound to a porous membrane or filter to which a liquid sample is added. As the liquid flows through the membrane, target analyte (such as an anti-folic acid antibody) binds to the capture reagent. The addition of sample is followed by (or made concurrent with) addition of detector reagent, such as labeled antibody (e.g., gold-conjugated or colored latex particle-conjugated protein). Alternatively, the detector reagent may be placed on the membrane in a manner that permits the detector to mix with the sample and thereby label the analyte. The visual detection of detector reagent provides an indication of the presence of target analyte in the sample. Representative flow-through assay devices are described in U.S. Pat. Nos. 4,246,339; 4,277, 560; 4,632,901; 4,812,293; 4,920,046; and 5,279,935; U.S. Patent Application Publication Nos. 20030049857 and 20040241876; and WO 08/030,546. Migration assay devices usually incorporate within them reagents that have been attached to colored labels, thereby permitting visible detection of the assay results without addition of further substances. See, for example, U.S. Pat. No. 4,770,853; PCT Publication No. WO 88/08534.

There are a number of commercially available lateral flow type tests and patents disclosing methods for the detection of large analytes (MW greater than 1,000 Daltons). U.S. Pat. No. 5,229,073 describes a semiquantitative competitive immunoassay lateral flow method for measuring plasma lipoprotein levels. This method utilizes a plurality of capture zones or lines containing immobilized antibodies to bind both the labeled and free lipoprotein to give a semi-quantitative result. In addition, U.S. Pat. No. 5,591,645 provides a chromatographic test strip with at least two portions. The first portion includes a movable tracer and the second portion includes an immobilized binder capable of binding to the analyte. Additional examples of lateral flow tests for large analytes are disclosed in the following patent documents: U.S. Pat. Nos. 4,168,146; 4,366,241; 4,855,240; 4,861,711; and 5,120,643; WO 97/06439; WO 98/36278; and WO 08/030,546.

Devices described herein generally include a strip of absorbent material (such as a microporous membrane), which, in some instances, can be made of different substances each joined to the other in zones, which may be abutted and/or overlapped. In some examples, the absorbent strip can be fixed on a supporting non-interactive material (such as nonwoven polyester), for example, to provide increased rigidity to the strip. Zones within each strip may differentially contain the specific binding partner(s) and/or other reagents required for the detection and/or quantification of the particular analyte being tested for, for example, the anti-folic acid antibody described herein. Thus these zones can be viewed as functional sectors or functional regions within the test device.

In general, a fluid sample is introduced to the strip at the proximal end of the strip, for instance by dipping or spotting. A sample is collected or obtained using methods well known to those skilled in the art. The sample containing the particular antibodies to be detected may be obtained from any biological source. In a particular example, the biological source is serum. The sample may be diluted, purified, concentrated, filtered, dissolved, suspended or otherwise manipulated prior to assay to optimize the immunoassay results. The fluid migrates distally through all the functional regions of the strip. The final distribution of the fluid in the individual functional regions depends on the adsorptive capacity and the dimensions of the materials used.

Another common feature to be considered in the use of assay devices is a means to detect the formation of a complex between an analyte (such as an anti-folic acid antibody described herein) and a capture reagent (such as folic acid, a folic acid protein conjugate or a fragment or chemical analog of folic acid). A detector (also referred to as detector reagent) serves this purpose. A detector may be integrated into an assay device (for example includes in a conjugate pad), or may be applied to the device from an external source.

A detector may be a single reagent or a series of reagents that collectively serve the detection purpose. In some instances, a detector reagent is a labeled binding partner specific for the analyte (such as a gold-conjugated immunoglobulin molecule). Thus, the detector can be a labeled second antibody that specifically binds the anti-folic acid antibody. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

In certain embodiments, the detection of test results may be visualized directly, or may be measured using a reader (such as a scanner). The reader device may detect color, fluorescence, luminescence, radioactivity, or any other detectable marker derived from the labeled reagent from the readout area (for example, the test line and/or control line).

In another embodiment of a lateral flow device, there may be a second (or third, fourth, or more) test line located parallel or perpendicular (or in any other spatial relationship) to test line in test result zone.

In one embodiment, a comparison of the control line to the test line yields the test result. In some instances, a valid result occurs when the control line is detected at a higher intensity level than the test line. For example, a valid result occurs when the control line is at least 5% or more, for example, 10%, 20%, 30%, 40%, 50%, 60%, 70%, 80%, 90%, 100% or more darker than the test line. In some instances, a valid result occurs when the control line is at least 0.5 fold or more, for example, 1 fold, 2 fold, 3 fold, 4 fold, 5 fold, 6 fold, 7 fold, 8 fold, 9 fold, 10 fold or more darker than the test line.

In one embodiment, the control line is a reference line that insures that the test has been run correctly. In one embodiment, the device of the invention is useful in the diagnosis of anti-folic acid antibodies in a sample when the control line is detected at an at least equal intensity as the test line. In some instances, if the test line is not at least equal in darkness or intensity as the control line then the test is said to have an invalid result. If the test line is at least equal or lighter than the control line then the testis said to have a valid result.

Kits

The present invention also pertains to kits useful in the methods of the invention. Such kits comprise various combinations of components useful in any of the methods described elsewhere herein, including for example, materials for assaying for the presence of anti-folic acid antibodies, and instructional material.

In one embodiment, the kit comprises a reagent for detecting the presence of antibodies to folic acid in a biological sample of a subject. In some embodiments, the biological sample is blood, urine, saliva, milk or plasma. In one embodiment, the biological sample comprises serum.

In one embodiment, folic acid or a folic acid protein conjugate is provided in a solubilized or freeze-dried form. Therefore, in one embodiment, a kit of the invention may further comprise one or more solutions for resuspension and dilution of the folic acid protein conjugate. In one embodiment, a solution for resuspension and dilution of a folic acid protein conjugate comprises a printing buffer. In one embodiment, a kit providing folic acid or a folic acid protein conjugate in a solubilized or freeze-dried form further comprises a substrate suitable for attachment of the folic acid or a folic acid protein conjugate.

In one embodiment, the kit of the invention further comprises a labeled biomolecule. In one embodiment, the labeled biomolecule is a labeled immunoglobulin antibody that binds antibodies bound to the folic acid deposited on the substrate. In one embodiment, a kit of the invention comprises one or more of anti-human IgG, anti-human IgM and anti-mouse IgG. In one embodiment, the labeled IgG immunoglobulin antibody is a labeled IgG1, labeled IgG2, labeled IgG3, or labeled IgG4 immunoglobulin antibody. In one embodiment, the label is selected from the group consisting of fluorescent dye, a cyanine dye, Digoxigenin, anti-Digoxigenin, alkaline phosphatase, peroxidase, avidin, streptavidin or biotin. In one embodiment, a cyanine dye is one of Cy®3 and Cy® 5.

In one embodiment, a substrate for the labeled biomolecule may also be provided in a kit of the invention. Generally, a substrate for the labeled immunoglobulin antibody includes but is not limited to a chemiluminescent or a fluorescent phosphatase or a peroxidase substrate or a fluorescent dye labeled with Digoxigenin, anti-Digoxigenin, biotin, avidin or streptavidin.

In one embodiment, a kit of the invention is an immunoassay kit. In various embodiments, an immunoassay kit may contain one or more of monoclonal antibodies and anti-antibody immunoglobulins. The monoclonal antibodies and the anti-antibody immunoglobulins can be provided in an amount of about 0.001 mg to 100 grams, and more preferably about 0.01 mg to 1 gram. The anti-antibody immunoglobulin may be a polyclonal immunoglobulin, protein A or protein G or functional fragments thereof, which may be labeled prior to use by methods known in the art. In several embodiments, the immunoassay kit includes one or more control antibodies. In one embodiment, a control antibody specifically binds a folic acid component as disclosed herein.

Point of Care Diagnostic and Risk Assessment Systems

The device of the invention can be applied to a point-of-care scenario. U.S. Pat. Nos. 6,267,722, 6,394,952 and 6,867,051 disclose and describe systems for diagnosing and assessing certain medical risks, the contents of which are incorporated herein. The devices are designed for use on site at the point of care, where patients are examined and tested, as well as for operation remote from the site. The systems are designed to accept input in the form of patient data, including, but not limited to biochemical test data, physical test data, historical data and other such data, and to process and output information, such as data relating to a medical diagnosis or a disease risk indicator. The patient data may be contained within the system, such as medical records or history, or may be input as a signal or image from a medical test or procedure, for example, immunoassay test data, blood pressure reading, ultrasound, X-ray or Mill, or introduced in any other form. Specific test data can be digitized, processed and input into the medical diagnosis expert system, where it may be integrated with other patient information. The output from the system is a disease risk index or medical diagnosis.

Point of care testing refers to real time diagnostic testing that can be done in a rapid time frame so that the resulting test is performed faster than comparable tests that do not employ this system. In addition, point of care testing refers to testing that can be performed rapidly and on site, such as in a doctor's office, at a bedside, in a stat laboratory, emergency room or other such locales, particularly where rapid and accurate results are required.

In an exemplary embodiment, a point of care diagnostic and risk assessment system includes a reader for reading patient data, a test device designed to be read in the reader, and software for analysis of the data. A test strip device in a plastic housing is designed for use with the reader, optionally including a symbology, such as an alphanumeric character bar code or other machine-readable code, and software designed for analysis of the data generated from the test strip are also provided.

In one embodiment, a reader refers to an instrument for detecting and/or quantitating data, such as on test strips. The data may be visible to the naked eye, but does not need to be visible. Such readers are disclosed and described in the above-incorporated U.S. Pat. Nos. 6,267,722, 6,394,952 and 6,867,051. A reflectance reader refers to an instrument adapted to read a test strip using reflected light, including fluorescence, or electromagnetic radiation of any wavelength. Reflectance can be detected using a photodetector or other detector, such as charge coupled diodes (CCD). An exemplary reflectance reader includes a cassette slot adapted to receive a test-strip, light-emitting diodes, optical fibers, a sensing head, including means for positioning the sensing head along the test strip, a control circuit to read the photodetector output and control the on and off operation of the light-emitting diodes, a memory circuit for storing raw and/or processed data, and a photodetector, such as a silicon photodiode detector. It will be appreciated that a color change refers to a change in intensity or hue of color or may be the appearance of color where no color existed or the disappearance of color.

In one embodiment, a sample is applied to a diagnostic immunoassay test strip, and colored or dark bands are produced. The intensity of the color reflected by the colored label in the test region (or detection zone) of the test strip is, for concentration ranges of interest, directly proportional or otherwise correlated with an amount of analyte present in the sample being tested. The color intensity produced is read, in accordance with the present embodiment, using a reader device, for example, a reflectance reader, adapted to read the test strip. The intensity of the color reflected by the colored label in the test region (or detection zone) of the test strip is directly proportional to the amount of analyte present in the sample being tested. In other words, a darker colored line in the test region indicates a greater amount of analyte, whereas a lighter colored line in the test region indicates a smaller amount of analyte. The color intensity produced, i.e., the darkness or lightness of the colored line, is read using a reader device, for example, a reflectance reader, adapted to read the test strip.

A reflectance measurement obtained by the reader device is correlated to the presence and/or quantity of analyte present in the sample. The reader takes a plurality of readings along the strip, and obtains data that are used to generate results that are an indication of the presence and/or quantity of analyte present in the sample. The system may correlate such data with the presence of an anti-folic acid antibody, folate-associated condition or risk thereof.

In addition to reading the test strip, the reader may (optionally) be adapted to read a symbology, such as a bar code, which is present on the test strip or housing and encodes information relating to the test strip device and/or test result and/or patient, and/or reagent or other desired information. Typically the associated information is stored in a remote computer database, but can be manually stored. Furthermore, the symbology can be imprinted when the device is used and the information encoded therein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Folic Acid/B12 Beads Assay

Described herein is a bead-based assay for detecting an antibody to folic acid in a sample.

The materials and methods are now described
Preparation of FA-Beads

Folic acid was covalently linked to epoxide resin beads. Beads were selected to be about 50 µm in size to be compatible with desired detection methods including flow cytometry and microscopy. Unbound 100 uL folic acid/B12 was washed from beads 3 times. 1 mL of TBST was added to the beads and they were spun at 200×G for 1 minute. The TBST-supernatant was discarded. Beads were resuspended in 1 mL TBST.
Assay Sample for Anti-FA IgG Antibodies 20 µL beads were added to each desired well of a 96-well PCR plate. Serum samples to be assayed were diluted 1:50 in TBST. 80 µL of the diluted serum sample was added to a single well. Each plate contained multiple control wells. Negative control wells were provided PBS, -IgG, or -IgM serum. Positive control well were provided anti-folic acid IgG antibodies produced in mice. Plates were sealed and incubated overnight at 4° C. or for 1 hour at room temperature.

Plates incubated overnight were allowed to come to room temperature before continuing with the assay. Supernatant from the sample was carefully discarded and the beads were washed 3 times. Beads were washed with 200 µL TBST, spun at 200×G for 1 minute, and the supernatant was discarded. 50 µL TBST was then added to the beads.

50 µL labeled anti-human IgG (secondary antibody, diluted 1:500 in TBST), was then added to each well. For multi-detection, anti-mouse FITC-labeled antibody, anti-human IgM Cy® 3-labeled antibody, and anti-human IgG Cy® 5-labeled antibody were added to each well. Plates were sealed and incubated overnight at 4° C. or for 1 hour at room temperature. Supernatant from the sample was carefully discarded and the beads were washed 3 times. Beads were washed with 200 µL TBST, spun at 200×G for 1 minute, and the supernatant was discarded. 100 µL TBS was then added to the beads.

To detect binding of anti-FA antibodies to the beads, beads were imaged on a fluorescent microscope (10×) using the appropriate filters or assayed using flow cytometry.

The results are now described

Figure 2:
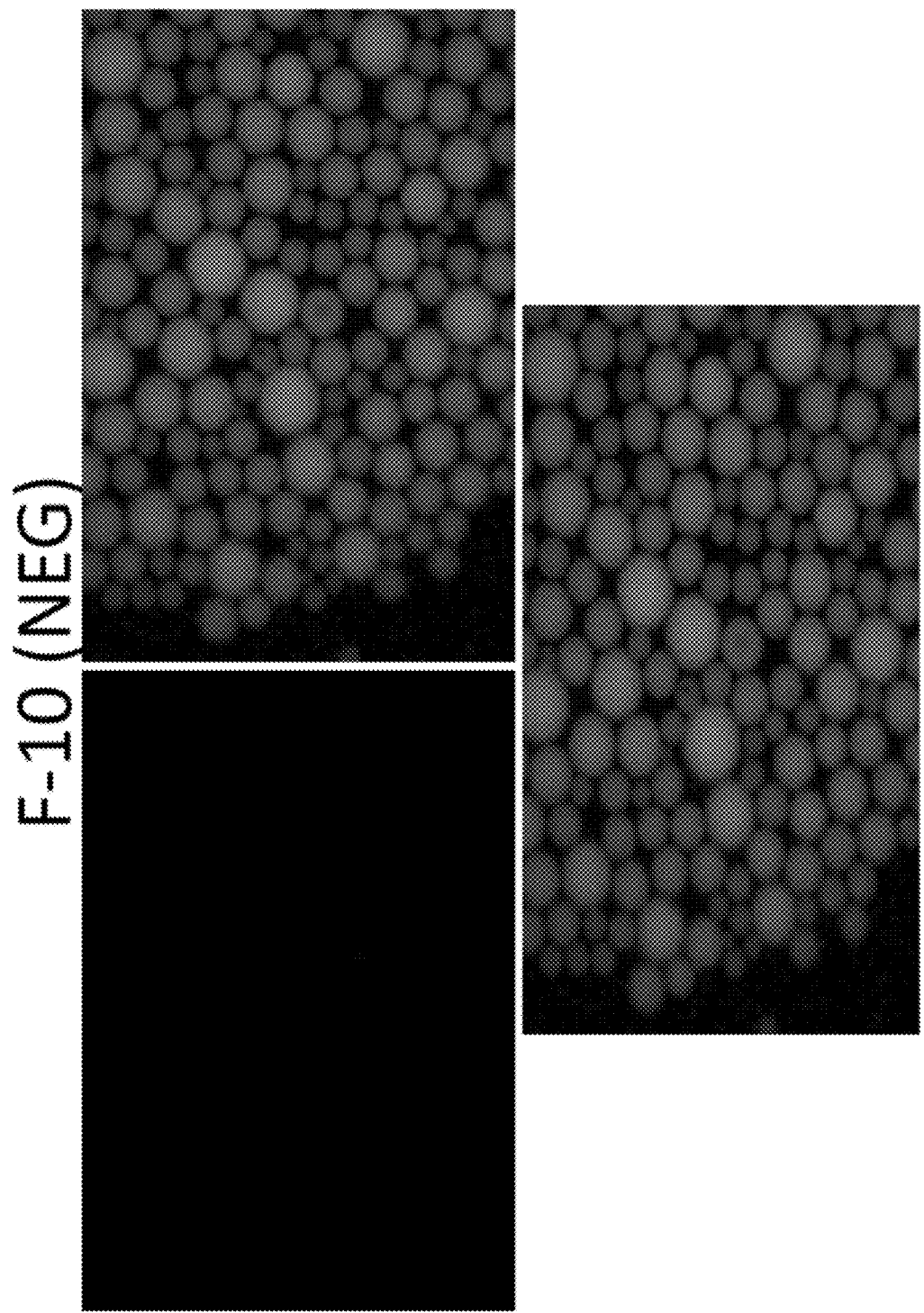
FIG. 2 depicts representative images of anti-IgG (red) binding in sample F10 from FIG. 1. This sample was negative for FA-reactive IgG antibodies.
Figure 3:
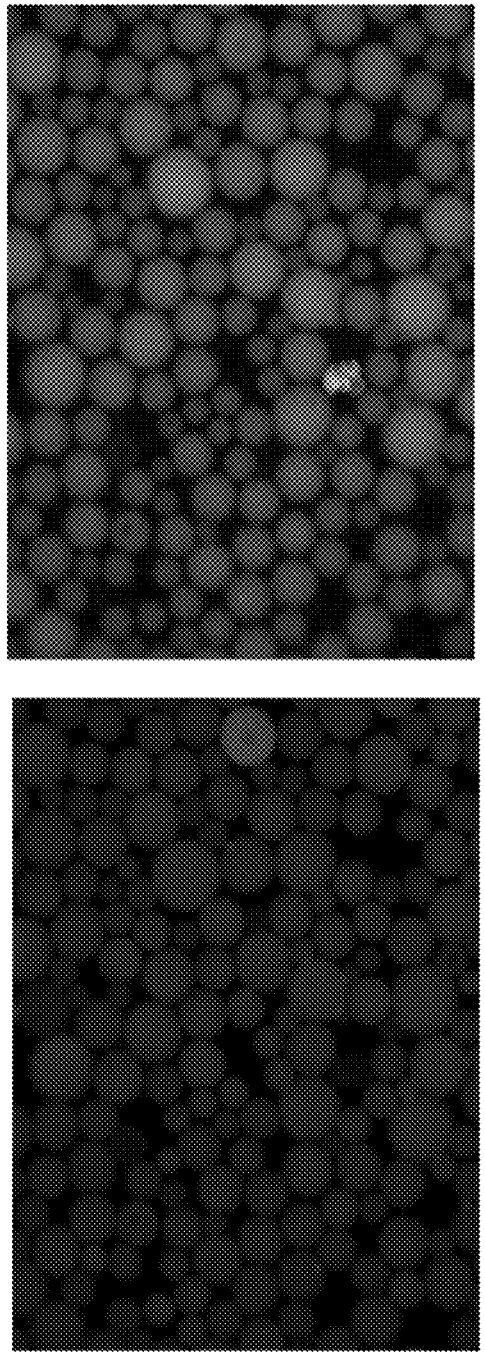
FIG. 3 depicts representative images of anti-IgG (red) binding in sample F5 from FIG. 1. This sample had low levels of FA-reactive IgG antibodies.
Figure 3:
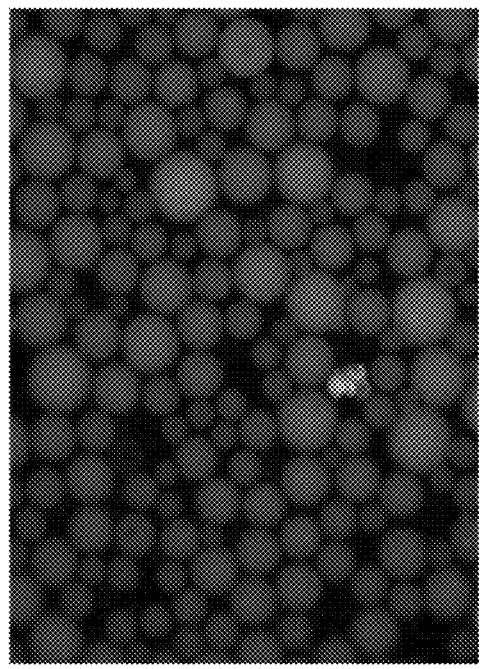
Figure 4:
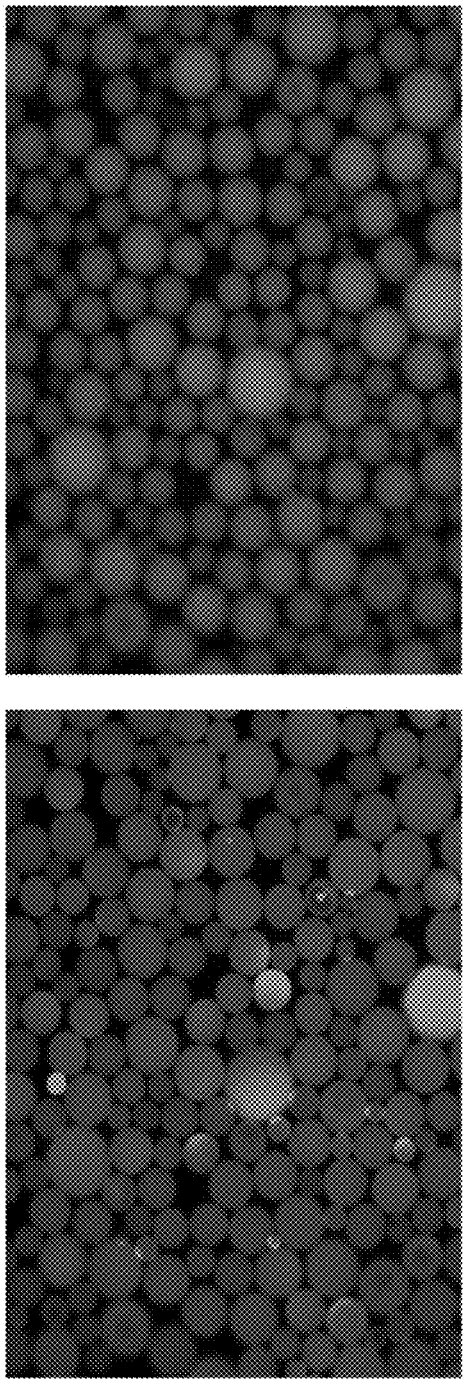
FIG. 4 depicts representative images of anti-IgG (red) binding in sample E6 from FIG. 1. This sample had high levels of FA-reactive IgG antibodies.
Figure 4:
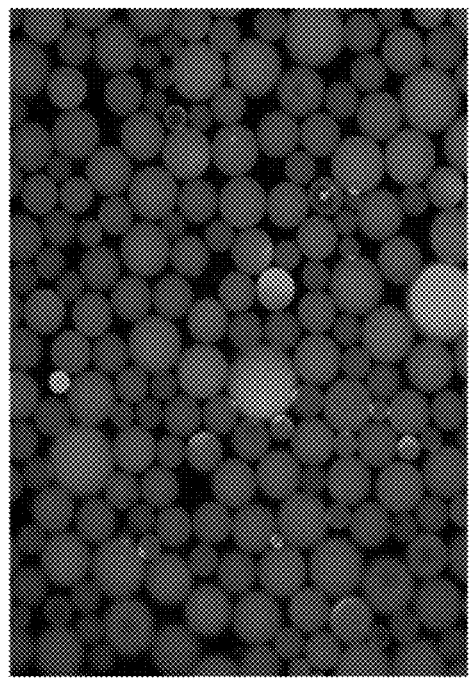

Seventy control samples were contacted with FA-beads in a 96-well plate. Blue squares represent wells containing a test sample. FIG. 1 depicts a heat map of IgG binding to FA-beads in control samples. FA is covalently linked to epoxide resin (54.4 μm±4.9). Shading of the blue squared indicates the level of IgG binding in the sample tested. Light blue represents negative IgG binding (e.g. FIG. 2), medium blue represents low levels of IgG binding (e.g. FIG. 3) and dark blue represents high levels of IgG binding (e.g. FIG. 4). Based on the results, it is estimated that 3-6% of the population has an IgG response to FA, which represents the portion of the population that is at risk of one or more FA-associated pathology.

Example 2: IgG/IgM Anti-Folic Acid Assay

Described herein is an assay for detecting an antibody to folic acid in a sample.

The materials and methods are now described

Preparation of Folic Acid Protein Conjugates (FA-KLH)

Folic acid (1 N-hydroxysuccinimide (25 μmol) and dicyclohexylcarbodiimide (50 μmol) were added to 200 μl of anhydrous dimethylformamide. The mixture was incubated at room temperature for 2 h, with shaking. The phases were separated by centrifugation (1000×G). The supernatant was added to a solution of keyhole limpet hemocyanin (KLH, 0.56 mg/mL). The mixture was incubated at room temperature for 4 h, with shaking, then dialyzed against 25 mM bicarbonate buffer and diluted to 1 mg/mL for printing or against water and freeze-dried for long term storage.

Preparation of Plates for Detection of Folic Acid-Antibody Interactions

The FA-KLH was diluted to 50 ng/μL in 25 mM bicarbonate with 2.5% glycerol. 1-2 μL of FA-KLH was added to the bottom center of each well in a COSTAR plate. The plate was covered with sticky film and incubated overnight at 4° C.

Serum samples were prepared in an untreated, U-bottom plate. For standard curve and positive controls anti-folic acid anti-bodies (mouse) were used. All samples were diluted 1:50 in TBS-T.

The FA-printed plate was washed 3 times with 100,200 and 200 TBST. 50 μL of diluted serum samples/antibodies were added to each well of the printed plate. The plate was covered with sticky film and incubated 2 hours at room temperature or overnight at 4° C. The plate was washed 3 times with 100,200 and 200 μL TBST. Anti-IgG-HRP (Invitrogen) was diluted to 1:2500 by serial dilution, or anti-IgM-HRP (Sigma) to 1:1000. Anti-human Ig-HRP was used for human serum samples. Anti-mouse Ig-HRP was used for positive controls and mouse serum samples. 50 μL of the appropriate antibody was added to each well. The plate was incubated for 1 hour at room temp. The plate was washed 3 times with 100, 200 and 200 μL TBST followed by 2 times with 200 and 200 μL TBS. 50 μL of femto (SuperSignal ELISA Femto Maximum sensitivity substrate, Thermo Scientific) reagent was added to each well. To detect binding of anti-FA antibodies, plates were imaged on a fluorescent microscope (10×), and images were captured at 30, 60 and 180 s exposure times.

Example 3: Population Characteristics of Anti-Folate Antibodies

Described herein is an analysis of the population characteristics of anti-folate antibodies.

197 individuals were tested for the presence of anti-folate antibodies including 94 males and 103 females. The ages of the individuals in the population tested ranged from 20 to 86.44 years, with an average of 58.7 years (standard deviation of 16.4 years). The average age of the males and females were 58.2 years (STDEV 16.5) and 59.1 years (STDEV 16.4) respectively.

Figure 5:
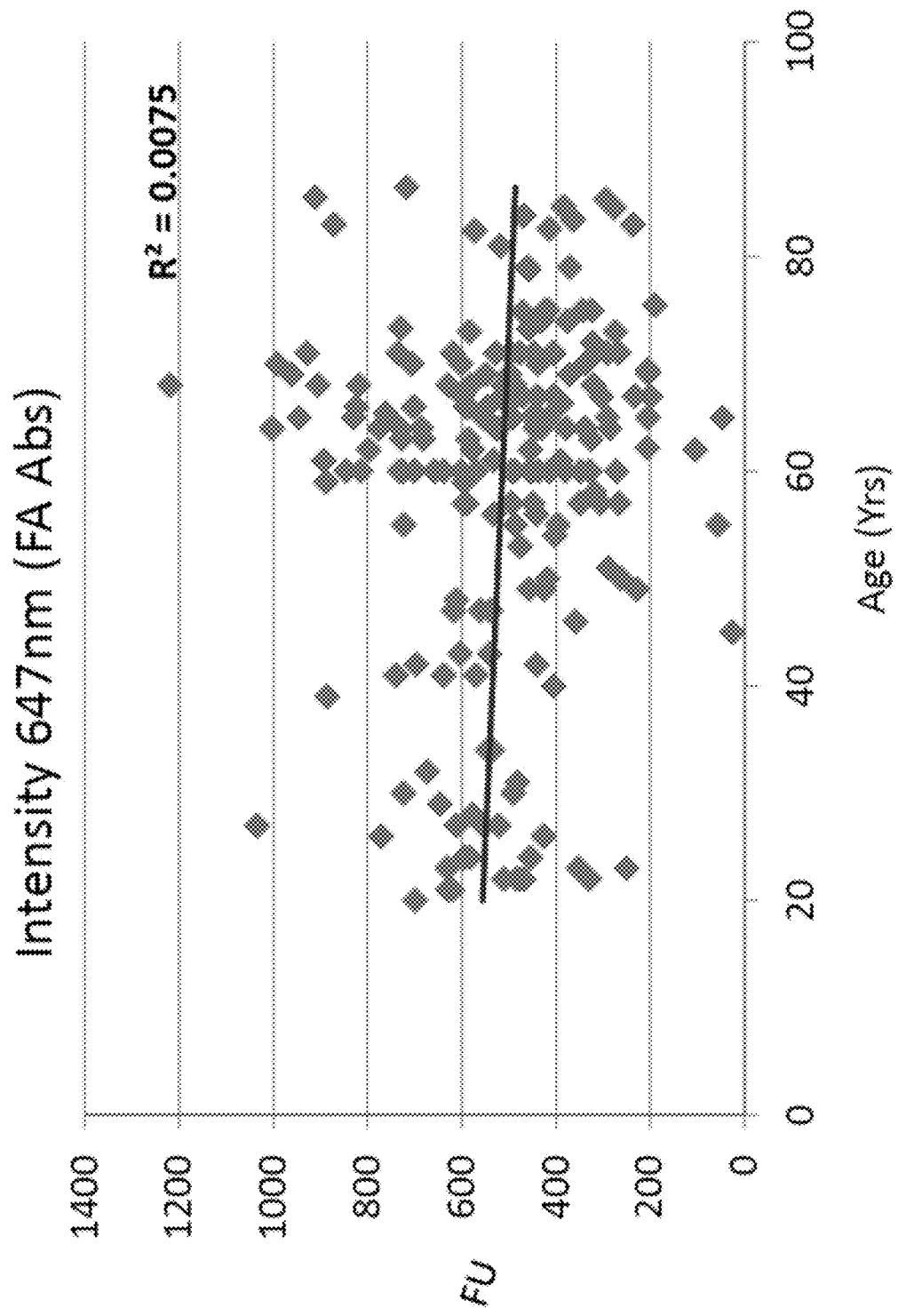
FIG. 5 depicts the results of an exemplary experimental analysis demonstrating the distribution of folic acid antibodies in a control population of males and females according to age.
Figure 6:
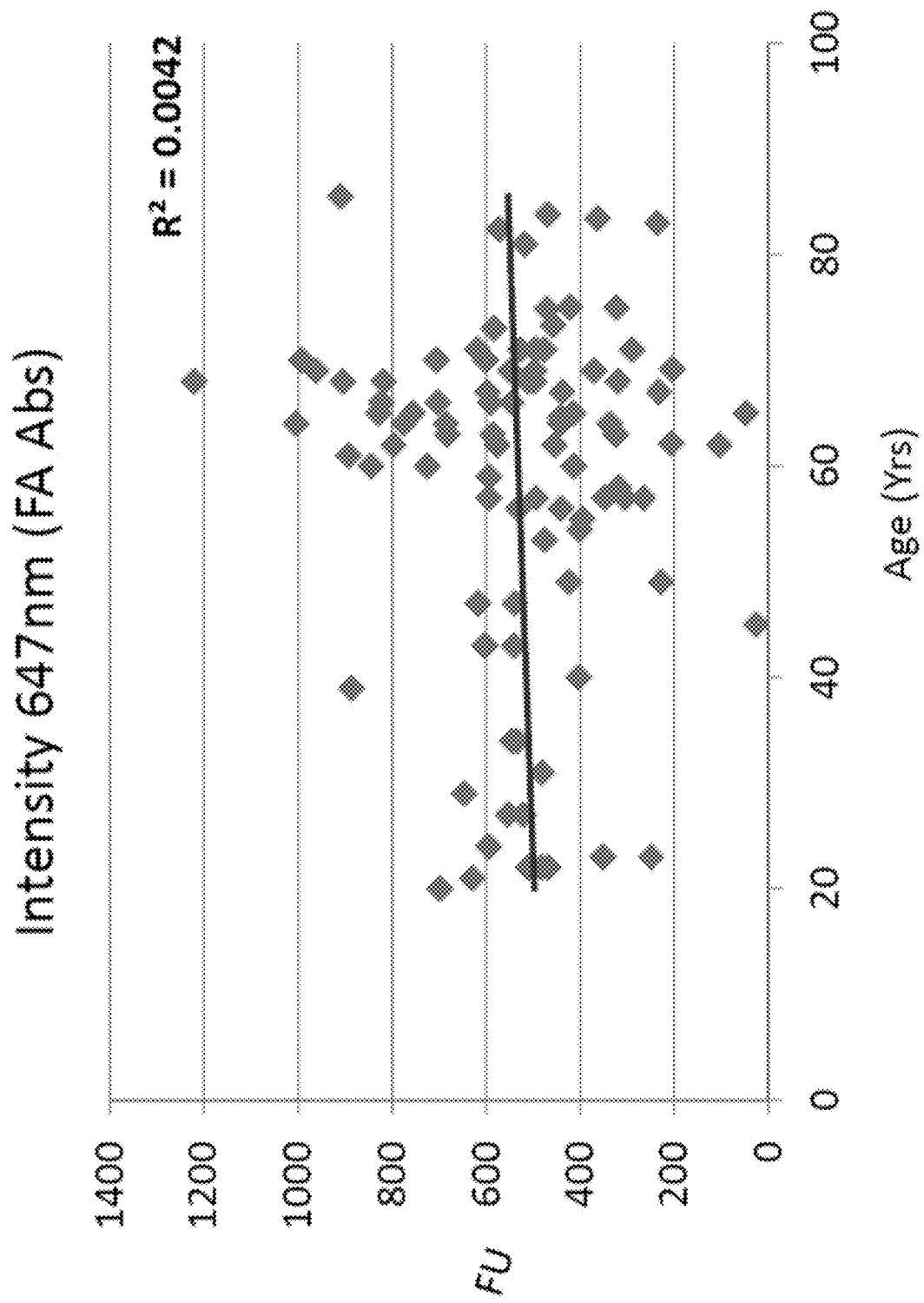
FIG. 6 depicts the results of an exemplary experimental analysis demonstrating the distribution of folic acid antibodies in a control population of males according to age.
Figure 7:
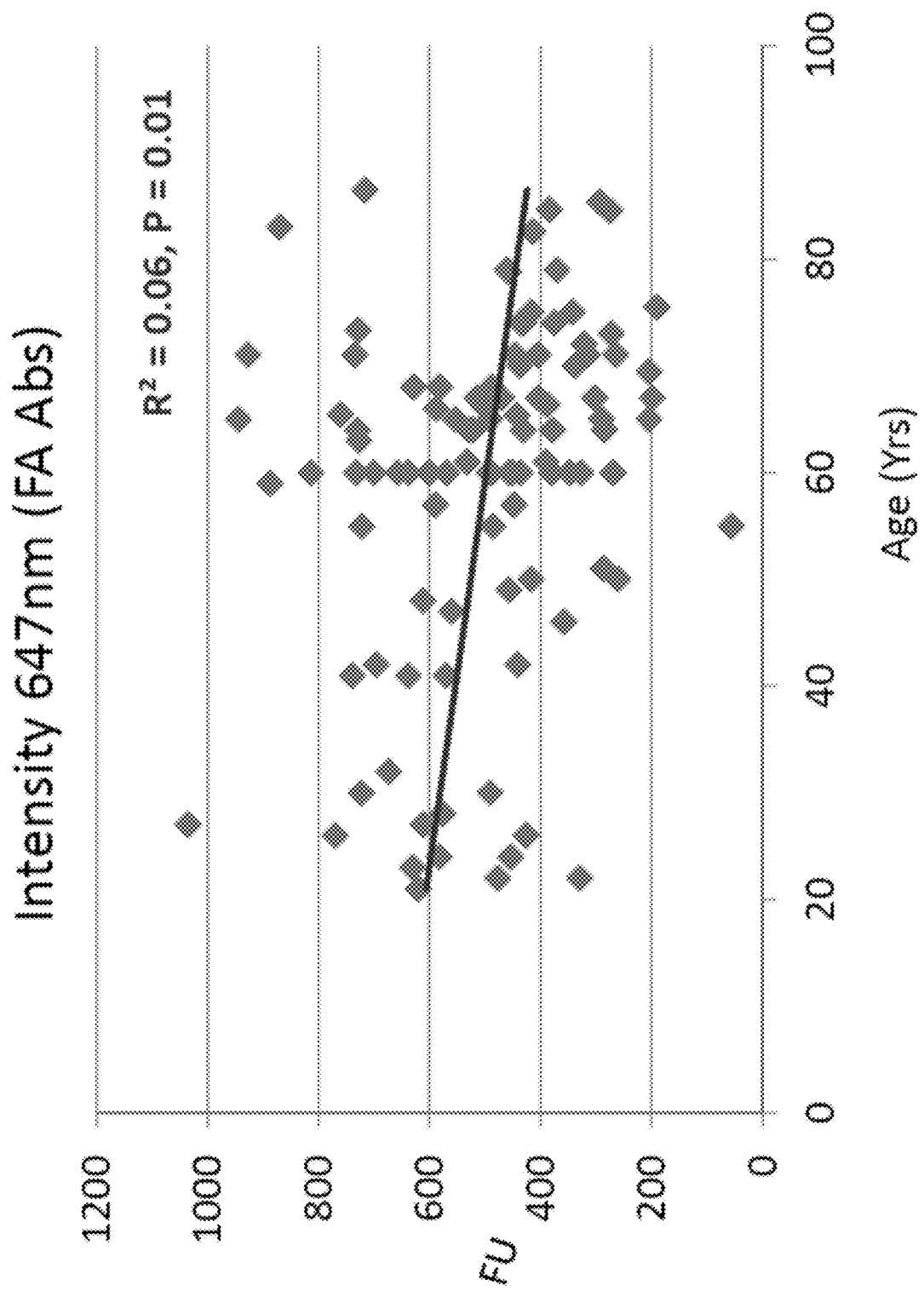
FIG. 7 depicts the results of an exemplary experimental analysis demonstrating the distribution of folic acid antibodies in a control population of females according to age.

FIG. 5 through FIG. 7 show the distributions of FA antibodies in the entire population, the male subset and the female subset respectively by age. FIG. 7 shows that women of "childbearing" age (20-40 years) have a significantly higher level of FA antibodies on average (average IgG fluorescence=600.2) than that of women of "postmenopausal" age (60-86.22 years; average IgG fluorescence=477.5). (P value<0.05). In addition there was a significant inverse association with aging in women and folic acid IgG antibody.

Figure 8:
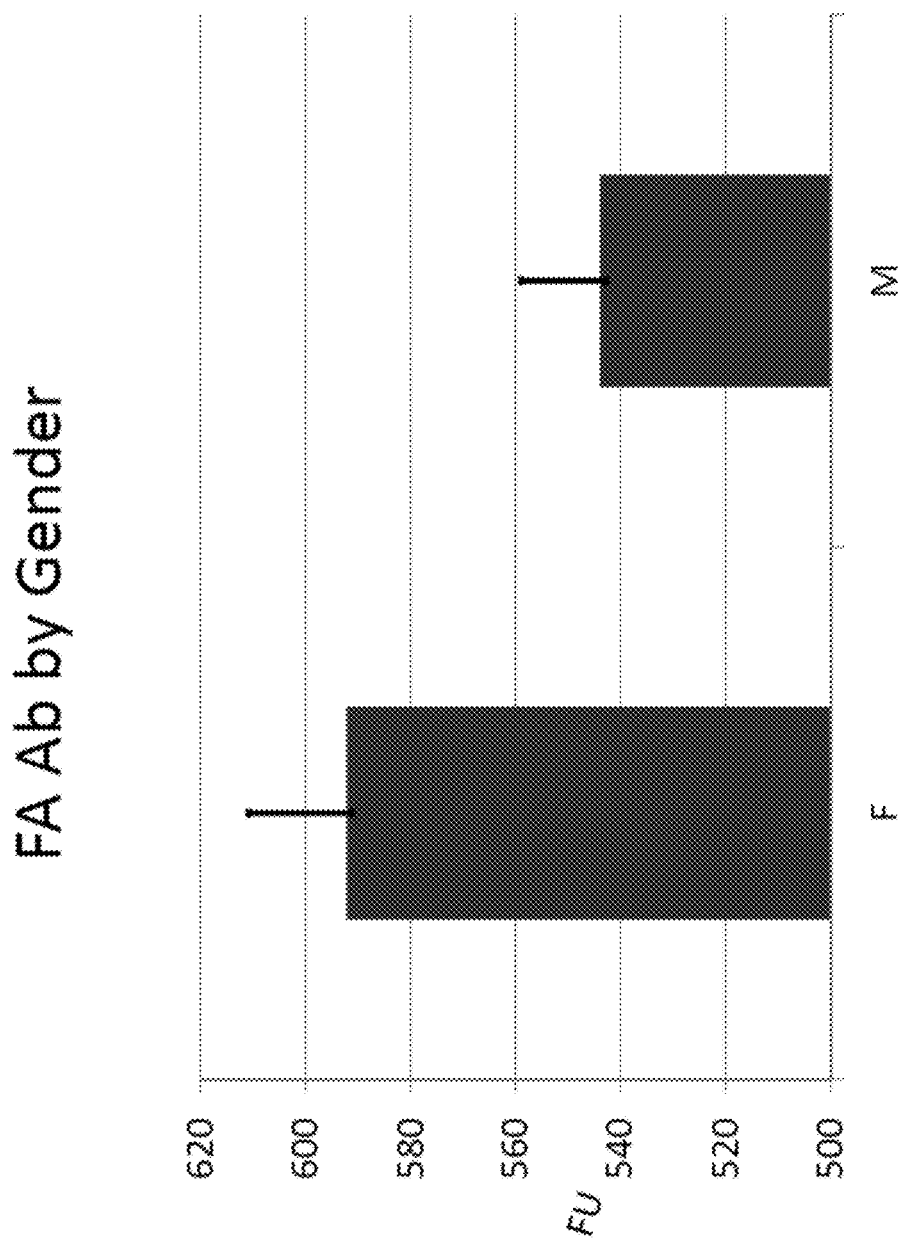
FIG. 8 depicts the results of an exemplary experimental analysis demonstrating the average IgG fluorescence of the male and female populations analyzed in FIGS. 6 and 7 respectively.

FIG. 8 shows that there is a significant difference in male vs female IgG (P=0.02), with the average male IgG fluorescence=543.8 (STDEV 146) and the average female IgG fluorescence=592.3 (STDEV 189.5).

These data support that the segment of the population most commonly consuming supplemental folic acid, i.e. women of childbearing age, have the highest prevalence of producing an immune response to folic acid.

Example 4: Antibodies to Folic Acid in Subjects with Major Depressive Disorder (MDD)

Autoimmunity can produce systemic and neurological manifestations and one of the novel autoantigens associated with neurological pathologies is folate receptor (FOLR1). This post-hoc analysis used depression samples from inadequate responders to selective serotonin reuptake inhibitors (SSRIs). This study examined associations of antibodies to folic acid in comparison to binding and blocking autoantibodies to FOLR1 in the serum of patients with major depressive disorder (MDD).

The materials and methods are now described

FOLR1 was immobilized to microtiter plates and used to determine anti-FOLR1 autoantibodies (IgG and IgM) in clinical serum samples. Patient samples (N=78) were obtained from a double-blind, randomized, placebo-controlled clinical trial of MDD patients and matched to control samples. Autoantibodies to FOLR1 and serum blocking of folate to FOLR1 binding were examined for association with MDD. Folic acid was immobilized to agarose beads and used to determine anti-folic acid antibodies (IgG) in clinical serum samples. Antibodies to folic acid were examined for association with MDD. Correlations were also examined between age and autoantibodies to FOLR1, serum blocking of folate to FOLR1, and antibodies to folic acid.

The results are now described

Elevated concentrations of anti-FOLR1 autoantibodies were found in depressed samples compared to the controls. The blocking of folate binding to FOLR1 was significantly higher for the case serum than matched controls (OR=2.16, 95% CI: 1.02-4.66, P value=0.004). There was a non-significant increase in IgG auto-antibodies, and a significantly higher IgM antibody concentration in the serum samples for cases than matched controls (OR=4.21, 95% CI: 1.98-9.46, P-value<0.001). The concentration of IgG binding of folic acid was significantly lower for the case serum than matched controls (P value<0.0001). This resulted in a highly significant decrease in the odds ratio (OR=0.054, CI: 0.018-0.1623, P<0.0001).

FIG. 9 provides a table showing IgG anti-folic (FA) acid antibodies (Abs) and blocking, IgG, or IgM autoantibodies to FOLR1 in serum of MDD matched cases and controls (Total=78 Cases, 78 Controls; Females=55 cases, 55 controls). The odds ratios for all other measures were calculated based on control data. The 50th percentile was used to threshold FA Abs because only one sample was positive in cases using the lower 25th percentile of FA Ab control signal distribution. The odds ratios for all other measures were calculated based on positive control data (positive=upper 25 percentile).

FIG. 10 provides a table showing correlations between immunologic measurements and age in cases and controls. Pearson's correlations are shown for each variable compared to age in all cases, all controls, and males and females from each population. Significant inverse correlations with age (P<0.05) were found only in control populations, and predominately in female controls for all measurements.

A previously established immunological assay for determining anti-IgG and anti-IgM autoantibodies to FOLR1 indicates that IgM autoantibodies and serum blocking of folate binding are associated with SSRI-resistant MDD. Specifically, blocking and IgM autoantibodies demonstrated a four-fold increase in risk. The newly established assay for measuring anti-folic acid antibodies is consistent with a protective effect. Specifically, IgG antibodies against folic acid demonstrated an 18-fold decrease in risk. This new assay promises to further our understanding of neurological diseases such as depression and to provide a better understanding of the role of the immunity and autoimmunity in this disease.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of diagnosing an infant or unborn child with a folate responsive birth defect or identifying an infant or unborn child at risk of developing a folate responsive birth defect comprising the steps of
   a) obtaining a sample;
   b) detecting an increased level of anti-folic acid antibodies in the sample as compared to a comparator control;
   c) diagnosing the infant or unborn child as having a folate responsive birth defect or at risk of developing a folate responsive birth defect; and
   d) treating, reducing, or delaying the folate responsive birth defect in the infant or unborn child, wherein anti-folic acid antibodies have been identified in the sample, comprising administering to the infant or the unborn child a folic acid based treatment.

2. The method of claim 1, wherein the sample is a serum sample of the infant or unborn child.

3. The method of claim 1, wherein the sample is a maternal serum sample.

4. The method of claim 1 wherein the folate responsive birth defect is selected from the group consisting of: neural tube defects, heart defects, outflow track defects, septal defects, patent ductus arteriosus, craniofacial defects, gastrointestinal defects, ocular defects, and limb abnormalities.

5. The method of claim 1, wherein the folate responsive birth defect is one or more of cerebral folate deficiency and hereditary folate malabsorption syndrome.

6. The method of claim 1, wherein the folic acid based treatment is one of folic acid, naturally occurring folate and 5MTHF.

* * * * *